US007871779B2

(12) United States Patent
Morrison et al.

(10) Patent No.: US 7,871,779 B2
(45) Date of Patent: *Jan. 18, 2011

(54) **MOLECULAR IDENTIFICATION OF *ASPERGILLUS* SPECIES**

(75) Inventors: Christine J. Morrison, Decatur, GA (US); Hans Peter Hinrikson, Wallisellen (CH)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 257 days.

This patent is subject to a terminal disclaimer.

(21) Appl. No.: 12/115,493

(22) Filed: May 5, 2008

(65) Prior Publication Data
US 2008/0227108 A1 Sep. 18, 2008

Related U.S. Application Data

(62) Division of application No. 10/514,861, filed on Nov. 16, 2004.

(60) Provisional application No. PCT/US03/16076, filed on May 16, 2003, now Pat. No. 7,384,741, provisional application No. 60/381,463, filed on May 17, 2002.

(51) Int. Cl.
   C12Q 1/68      (2006.01)
   C12P 19/34     (2006.01)
   C07H 21/04     (2006.01)
(52) U.S. Cl. .................. 435/6; 435/91.2; 536/23.7; 536/24.32
(58) Field of Classification Search .................. None
   See application file for complete search history.

(56) References Cited

U.S. PATENT DOCUMENTS

| | | | |
|---|---|---|---|
| 5,827,695 A | 10/1998 | Beck | |
| 6,287,779 B1 | 9/2001 | Engel et al. | |
| 6,372,430 B1 | 4/2002 | Morrison et al. | |
| 6,872,523 B1 | 3/2005 | Iwen et al. | |

FOREIGN PATENT DOCUMENTS

| | | |
|---|---|---|
| WO | WO 98/50584 | 11/1998 |
| WO | WO 00/73499 A2 | 7/2000 |
| WO | WO 03/097815 A3 | 11/2003 |

OTHER PUBLICATIONS

Borsuk et al., *Acta Biochimica Polincia*, 41, 1:73-77, (1994).
GenBank Accession No. AM176692, (Dec. 13, 2005).
Mail.—J. and Rogers, S.O., Environmental Forrest Biology, University of New York, College of Environmental Science and Forestry, (Apr. 28, 2000), see the Office action from U.S. Appl. No. 10/514,861, dated Jul. 6, 2007.

Nikkuni et al., *J. Gen. Appl. Microbiol.*, 44:225-230, (1998).
White et al., "PCR Protocols: A Guide to Methods and Application," p. 315-322, (1990), see the Office action from U.S. Appl. No. 10/514,861, dated Jul. 6, 2007.
Botelho and Planta, "Specific Identification of *Candida albicans* by Hybridization with Oligonucleotides Derived from Ribosomal DNA Internal Spacers," *Yeast* 10:709-717 (1994).
Bowie et al., *Science*, 257:1306-1310, (1990).
Chen et al., "Polymorphic Internal Transcribed Spacer Region 1 DNA Sequences Identify Medically Important Yeasts," *J. Clinical Microbiology* 39(11):4042-4051 (Nov. 2001).
Einsele et al., "Detection and Identification of Fungal Pathogens in Blood by Using Molecular Probes," *J. Clin. Microbiol.* 35:1353-1360 (1997).
Eisner et al., "A PCR Method for Rapid Identification of Clinically Significant Yeast Species Using ITS1 & ITS2 Sequence Polymorphisms," 2000 General Meeting (May 21, 2000 through May 25, 2000), American Society for Microbiology (Abstract).
Elie et al., "Rapid Identification of *Candida* Species with Species-Specific DNA Probes," *J. Clin. Microbiol.* 36:3260-3265 (1998).
EMBL database, Accession No. AJ001336, (Aug. 27, 1997).
Fujita et al., "Microtitration Plate Enzyme Immunoassay To Detect PCR-Amplified DNA from *Candida* Species in Blood," *J. Clin. Microbiol.* 33:962-967 (1995).
Gaskell et al., "Analysis of the Internal Transcribed Spacer Regions of Ribosomal DNA in Common Airborne Allergenic Fungi," *Electrophoresis* 18:1567-1569 (1997).
Gaskell et al., "Analysis of the internal transcribed spacer regions of ribosomal DNA in common airborne allergenic fungi," *Electrophoresis* 18:1567-1569 (1997).
Haugland et al., "Quantitative PCR Analysis of Selected *Aspergillus*, *Penicillium* and *Paecilomyces* Species," *Syst. Appl. Microbiol.* 27:198-210 (2004).
Henry et al., "Identification of *Aspergillus* Species Using Internal Transcribed Spacer Regions 1 and 2," *J. Clinical Microbiology* 38(4):1510-1515 (Apr. 2000).

(Continued)

*Primary Examiner*—Larry R Helms
*Assistant Examiner*—Padma V Baskar
(74) *Attorney, Agent, or Firm*—Klarquist Sparkman, LLP

(57) ABSTRACT

Novel techniques for the detection of *Aspergillus* in samples are disclosed. These techniques relate to PCR amplification and/or detection of *Aspergillus* ITS1 rDNA sequences, and the identification of particular species of *Aspergillus* by detecting differences in the ITS1-V1, ITS-V2, ITS-V3, ITS-V4, and ITS-V5 nucleic acid sequences of *Aspergillus*. The highly variable regions of the ITS1 rDNA sequences are particularly useful in distinguishing, for example, *Aspergillus clavatus*, *Aspergillus granulosus*, *Aspergillus sydowii*, *Aspergillus flavipes*, *Aspergillus restrictus*, *Aspergillus versicolor*, *Aspergillus wentii*, and *Aspergillus chevalieri*. In particular embodiments, the sequence differences are also able to distinguish among variants of particular species, such as *Aspergillus granulosus* CBS 119.5A, *Aspergillus granulosus* strain NRRL 1932, *Aspergillus sydowii* strain NRRL 250, *Aspergillus sydowii* strain NRRL 4768, *Aspergillus sydowii* strain CUH1, *Aspergillus sydowii* strain CUH2, *Aspergillus sydowii* strain CUH7, and *Aspergillus sydowii* strain CUH8.

19 Claims, 2 Drawing Sheets

OTHER PUBLICATIONS

Hinrikson et al., "Assessment of Ribosomal Large-Subunit D1-D2, Internal Transcribed Spacer 1, and Internal Transcribed Spacer 2 Regions as Targets for Molecular Identification of Medically Important *Aspergillus* Species," *J. Clinical Microbiology* 43(5):2095-2103 (May 2005).

Iwen et al., "Utilization of the internal transcribed spacer regions as molecular targets to detect and identify human fungal pathogens," *Medical Mycology* 40:87-109 (2002).

Kumeda and Asao, "Heteroduplex Panel Analysis, a Novel Method for Genetic Identification of *Aspergillus* Section *Flavi* Strains," *Appl. Environ. Microbiol.* 67:4084-4090 (2001).

Lindsley et al., "Rapid Identification of Dimorphic and Yeast-Like Fungal Pathogens Using Specific DNA Probes," *J. Clin. Microbiol.* 39:3505-3511 (2001).

Luo and Mitchell, "Rapid Identification of Pathogenic Fungi Directly from Cultures by Using Multiplex PCR," *J. Clin. Microbiol.* 40:2860-2865 (2002).

Mills et al., "Detection and Differentiation of Colletotrichum Gloeosporioides Isolates Using PCR," *FEMS Microbiol. Lett.* 98:137-143 (1992).

Pařenicová et al., "Combined Molecular and Biochemical Approach Identifies *Aspergillus japonicus* and *Aspergillus aculeatus* as Two Species," *Appl. Environ. Microbiol.* 67:521-527 (2001).

Peterson, S.W., "Phylogenetic Analysis of *Penicillium* Species Based on ITS and 1su-rDNA Nucleotide Sequences," pp. 163-178 in R.A. Samson and J.I. Pitt (eds.), Integration of Modern Taxonomic Methods for *Penicillium* and *Aspergillus* Classification, Harwood Academic Publishers, Amsterdam, The Netherlands (2000).

Tarcha et al., "Phylogenetic Analysis of the ITS1, 5.8S and ITS2 rDNA Sequences of *Lacazia loboi* Confirms the Placement of this Unique Fungal Pathogen with the Onygenales," 2001 General Meeting (May 20, 2001 through May 24, 2001), American Society for Microbiology (Abstract).

Uijthof et al., "Exophiala dermatitidis and Sarcinomyces phaeomuriformis: ITS1- Sequencing and Nutritional Physiology," *Med. Mycol.* 36:143-151 (1998).

Varga et al., "Molecular Analysis of Variability Within the Toxigenic *Aspergillus ochraceus* Species," *Can. J. Microbiol.* 46:593-599 (2000).

Varga et al., "Phylogenetic Analysis of *Aspergillus* Section *Circumdati* based on Sequences of the Internal Transcribed Spacer Regions and the 5.8 S rRNA Gene," *Fungal Genet. Biol.* 30:71-80 (2000).

White et al., "Amplification and Direct Sequencing of Fungal Ribosomal RNA Genes for Phylogenetics," *PCR Protocols: A Guide to Methods and Applications*, Academic Press, Inc., Ch. 38:315-321 (1990).

GenBank Accession No. AJ001337, "Aspergillus cf. Flavipes ATUS (USA) 5.8S rRNA Gene and ITS1 and ITS2 DNA," *EMBL Database*, (originated Aug. 27, 1997; updated Jul. 13, 2001).

Narutaki et al., "Identification of Fungi Based on the Nucleotide Sequence Homology of Their Internal Transcribed Spacer 1 (ITS1) Region," *PDA Journal of Pharmaceutical Science and Technology*, 56(2):90-98, (Mar.-Apr. 2002).

Zhao et al., "Identification of *Aspergillus fumigatus* and Related Species by Nested PCR Targeting Ribosomal DNA Internal Transcribed Spacer Regions," *Journal of Clinical Microbiology*, 39(6):2261-2266 (2001).

Fig. 2

SEQUENCE LISTING

<160> NUMBER OF SEQ ID NOS: 67

<210> SEQ ID NO 1
<211> LENGTH: 187
<212> TYPE: DNA
<213> ORGANISM: Aspergillus clavatus

<400> SEQUENCE: 1

```
ccgagtgcgg gccctctggg tccaacctcc cacccgtgtt tatcgtacct tgttgcttcg      60
gcgggcccgc cgtcttcgga cggccgccgg ggaggcctcc gcgccccgg gcccgcgccc       120 gccgaagacc acaacatgaa ctctgttctg aagttttgca gtctgagttg attatcataa     180
tcagtta                                                                187
```

<210> SEQ ID NO 2
<211> LENGTH: 156
<212> TYPE: DNA
<213> ORGANISM: Aspergillus granulosus

<400> SEQUENCE: 2

```
ccgagtgcag gtctgcccct gggcaggcct aacctcccac ccgtgaatac ctgaccaacg      60
ttgcttcggc ggtgcgcccc tccgggggca gccgccggag accacaccga acctcttgtt     120
taagcctgtt gtctgagctt gatagcaaat ctatta                                156
```

<210> SEQ ID NO 3
<211> LENGTH: 156
<212> TYPE: DNA
<213> ORGANISM: Aspergillus granulosus

<400> SEQUENCE: 3

```
ccgagtgcag gtctgcccct gggcaggcct aacctcccac ccgtgaatac ctgaccaacg      60
ttgcttcggc ggtgcgcccc tccgggggca gccgccggag accacaccga acctcttgtt     120
taagcctgtt gtctgagctt gatagcaaat ctatta                                156
```

<210> SEQ ID NO 4
<211> LENGTH: 155
<212> TYPE: DNA
<213> ORGANISM: Aspergillus sydowii

<400> SEQUENCE: 4

```
ctgagtgcgg gctgcctccg ggcgcccaac ctcccacccg tgaataccta acactgttgc      60
ttcggcgggg aaccccctcg ggggcgagcc gccgggact actgaacttc atgcctgaga      120
gtgatgcagt ctgagtctga atataaaatc agtca                                 155
```

<210> SEQ ID NO 5
<211> LENGTH: 155
<212> TYPE: DNA
<213> ORGANISM: Aspergillus sydowii

<400> SEQUENCE: 5
ctgagtgcgg gctgcctccg ggcgcccaac ctcccacccg tgaataccta acactgttgc     60
ttcggcgggg aaccccctcg ggggcgagcc gccggggact actgaacttc atgcctgaga    120
gtgatgcagt ctgagtctga atataaaatc agtca                                155

<210> SEQ ID NO 6
<211> LENGTH: 155
<212> TYPE: DNA
<213> ORGANISM: Aspergillus sydowii

<400> SEQUENCE: 6
ctgagtgcgg gctgcctccg ggcgcccaac ctcccacccg tgaataccta acactgttgc     60
ttcggcgggg aaccccctcg ggggcgagcc gccggggact actgaacttc atgcctgaga    120
gtgatgcagt ctgagtctga atataaaatc agtca                                155

<210> SEQ ID NO 7
<211> LENGTH: 155
<212> TYPE: DNA
<213> ORGANISM: Aspergillus sydowii

<400> SEQUENCE: 7
ctgagtgcgg gctgcctccg ggcgcccaac ctcccacccg tgaataccta acactgttgc     60
ttcggcgggg aaccccctcg ggggcgagcc gccggggact actgaacttc atgcctgaga    120
gtgatgcagt ctgagtctga atataaaatc agtca                                155

<210> SEQ ID NO 8
<211> LENGTH: 155
<212> TYPE: DNA
<213> ORGANISM: Aspergillus sydowii

<400> SEQUENCE: 8
ctgagtgcgg gctgcctccg ggcgcccaac ctcccacccg tgaataccta acactgttgc     60
ttcggcgggg agctccctcg ggggcgagcc gccggggact actgaacttc atgcctgaga    120
gtgatgcagt ctgagtctga atataaaatc agtca                                155

<210> SEQ ID NO 9
<211> LENGTH: 155
<212> TYPE: DNA
<213> ORGANISM: Aspergillus sydowii

<400> SEQUENCE: 9
ctgagtgcgg gctgcctccg ggcgcccaac ctcccacccg tgaataccta acactgttgc     60
ttcggcgggg aaccccctcg ggggcgagcc gccggggact actgaacttc atgcctgaga    120
gtgatgcagt ctgagtctga atataaaatc agtca                                155

<210> SEQ ID NO 10
<211> LENGTH: 185
<212> TYPE: DNA
<213> ORGANISM: Aspergillus flavipes

<400> SEQUENCE: 10

```
ccgagtgagg gtcctcgtgg cccaacctcc cacccgtgac tactgtacca ctgttgcttc      60
ggcgggcccg ccagcgtccg ctggccgccg gggggcttct gccccgggc cgtgcccgc       120 cggagacccc aacacgaaca ctgtttctga aagcctgtat gaattcgatt ctttgtaatc    180
agtta                                                                 185

<210> SEQ ID NO 11
<211> LENGTH: 184
<212> TYPE: DNA
<213> ORGANISM: Aspergillus flavipes

<400> SEQUENCE: 11
ccgagtgagg gtcctcgtgg cccaacctcc cacccgtgac tactgtacca ctgttgcttc      60
ggcgggcccg ccagcctagc tggccgccgg ggggcttctg ccccgggcc cgcgcccgcc     120 ggagacccca acacgaacac tgtttctgaa agcctgtatg aatccgattc tttgtaatca    180
gtta                                                                  184

<210> SEQ ID NO 12
<211> LENGTH: 185
<212> TYPE: DNA
<213> ORGANISM: Aspergillus flavipes

<400> SEQUENCE: 12
ccgagtgagg gtcctcgtgg cccaacctcc cacccgtgac tactgtacca ctgttgcttc      60
ggcgggcccg ccagcgcccg ctggccgccg ggggcttct gccccgggc cgtgcccgc       120 cggagacccc aacacgaaca ctgtttctga aagcctgtat gaatccgatt ctttgtaatc    180
agtta                                                                 185

<210> SEQ ID NO 13
<211> LENGTH: 181
<212> TYPE: DNA
<213> ORGANISM: Aspergillus restrictus

<400> SEQUENCE: 13
ccgagtgcgg gccctctggg tccaacctcc catccgtgtc tcttgtaccc tgttgcttcg      60
gcgggcccgc cttcatggcc gccggggggc ttctgccccc gggccgcgc cgccggaga      120 ctccaacatt gaacactgtc tgaaggttgc agtctgagtt ttcatataag aaaaatcgtt    180
a                                                                     181

<210> SEQ ID NO 14
<211> LENGTH: 181
<212> TYPE: DNA
<213> ORGANISM: Aspergillus restrictus

<400> SEQUENCE: 14
ccgagtgcgg gccctctggg tccaacctcc catccgtgtc tcttgtaccc tgttgcttcg      60
gcgggcccgc cttcatggcc gccggggggc ttctgccccc gggccgcgc cgccggaga      120 ctccaacatt gaacactgtc tgaaggttgc agtctgagtt ttcatataag aaaaatcgtt    180
a                                                                     181

<210> SEQ ID NO 15
<211> LENGTH: 155
<212> TYPE: DNA
<213> ORGANISM: Aspergillus versicolor

<400> SEQUENCE: 15
```

-continued

```
ctgagtgcgg gctgcctccg ggcgcccaac ctcccacccg tgactaccta acactgttgc    60
ttcggcgggg agccctctcg ggggcgagcc gccggggact actgaacttc atgcctgaga   120
gtgatgcagt ctgagtctga atataaaatc agtca                              155

<210> SEQ ID NO 16
<211> LENGTH: 155
<212> TYPE: DNA
<213> ORGANISM: Aspergillus versicolor

<400> SEQUENCE: 16
ctgagtgcgg gctgcctccg ggcgcccaac ctcccacccg tgactaccta acactgttgc    60
ttcggcgggg agccctctcg ggggcgagcc gccggggact actgaacttc atgcctgaga   120
gtgatgcagt ctgagtctga atataaaatc agtca                              155

<210> SEQ ID NO 17
<211> LENGTH: 155
<212> TYPE: DNA
<213> ORGANISM: Aspergillus versicolor

<400> SEQUENCE: 17
ctgagtgcgg gctgcctccg ggcgcccaac ctcccacccg tgactaccta acactgttgc    60
ttcggcgggg agccctctcg ggggcgagcc gccggggact actgaacttc atgcctgaga   120
gtgatgcagt ctgagtctga atataaaatc agtca                              155

<210> SEQ ID NO 18
<211> LENGTH: 155
<212> TYPE: DNA
<213> ORGANISM: Aspergillus versicolor

<400> SEQUENCE: 18
ccgagtgcgg gctgcctccg ggcgcccaac ctcccacccg tgactaccta acactgttgc    60
ttcggcgggg agccctctcg ggggcgagcc gccggggact actgaacttc atgcctgaga   120
gtgatgcagt ctgagtctga atataaaatc agtca                              155

<210> SEQ ID NO 19
<211> LENGTH: 178
<212> TYPE: DNA
<213> ORGANISM: Aspergillus wentii

<400> SEQUENCE: 19
ccgagtgagg acctaaccgg tccaacctcc cacccgtgtc tatcgtacct tgttgcttcg    60
gcgggcccgc cattcgtggc cgccgggggg catctcgccc ccgggcccgc gcccgccgga   120
gacaccaaca cgaacactgt ctgaaggttg cagtctgagt cgatttattt aatcgtta     178

<210> SEQ ID NO 20
<211> LENGTH: 142
<212> TYPE: DNA
<213> ORGANISM: Aspergillus chevalieri

<400> SEQUENCE: 20
ccgagtgcgg gccctctggg tccaacctcc catccgtgtc tatctgtacc ctgttgcttc    60
ggcgtggcca cggcccgccg gagactaaca tttgaacgct gtctgaagtt tgcagtctga   120 gttttagtt aaacaatcgt ta                                             142

<210> SEQ ID NO 21
```

<211> LENGTH: 142
<212> TYPE: DNA
<213> ORGANISM: Aspergillus chevalieri

<400> SEQUENCE: 21

```
ccgagtgcgg gccctctggg tccaacctcc catccgtgtc tatctgtacc ctgttgcttc    60
ggcgtggcca cggcccgccg gagactaaca tttgaacgct gtctgaagtt tgcagtctga    120
gtttttagtt aaacaatcgt ta                                             142
```

<210> SEQ ID NO 22
<211> LENGTH: 155
<212> TYPE: DNA
<213> ORGANISM: Aspergillus ustus

<400> SEQUENCE: 22

```
ccgagtgcag gtctgccccc gggcaggcct aacctcccac ccgtgaatac ctgaccaacg    60
ttgcttcggc ggtgcgcccc ccgggggta gccgccggag accacaccga acctcctgtc     120
tttagtgttg tctgagcttg atagcaaacc tatta                              155
```

<210> SEQ ID NO 23
<211> LENGTH: 155
<212> TYPE: DNA
<213> ORGANISM: Aspergillus ustus

<400> SEQUENCE: 23

```
ccgagtgcag gtctgccccc gggcaggcct aacctcccac ccgtgaatac ctgaccaacg    60
ttgcttcggc ggtgcgcccc tccgggggta gccgccggag accacattga acctcttgtc    120
tttagtgttg tctgagcttg atagcaaacc tatta                              155
```

<210> SEQ ID NO 24
<211> LENGTH: 161
<212> TYPE: DNA
<213> ORGANISM: Aspergillus ustus

<400> SEQUENCE: 24

```
ccgagtgcag gtctgccccc gggcaggcct aacctcccac ccgtgaatac ctgaccaacg    60
ttgcttcggc ggtgcgctcc ccccggggggc agccgccgga gaccacaccg aacctcttgt    120
tatagcgtgt cgtctgagct tgatacaagc aaacctaatt a                        161
```

<210> SEQ ID NO 25
<211> LENGTH: 172
<212> TYPE: DNA
<213> ORGANISM: Aspergillus ustus

<400> SEQUENCE: 25

```
ccgagtgcag gcctcgcccc acaggcaggc ctaacctccc accgtgaat acctgaccaa    60 cgttgcttcg gcgtgcgcg ccccttccc gggggcgta agccgccggg gaccacaccg     120
aacttcttgt ttttagcgtg tcgtctgagc ttgatacaag caaacctaat ta            172
```

<210> SEQ ID NO 26
<211> LENGTH: 156
<212> TYPE: DNA
<213> ORGANISM: Aspergillus ustus

<400> SEQUENCE: 26

```
ccgagtgcag gtctgccccc gggcaggcct aacctcccac ccgtgaatac ctgaccaacg    60
ttgcttcggc ggtgcgcccc ccccggggggt agccgccgga gaccacaccg aacctcctgt    120
```

-continued ctttagtgtt gtctgagctt gatagcaaac ctatta                          156

<210> SEQ ID NO 27
<211> LENGTH: 172
<212> TYPE: DNA
<213> ORGANISM: Aspergillus ustus

<400> SEQUENCE: 27
ccgagtgcag gcctcgcccc acaggcaggc ctaacctccc acccgtgaat acctgaccaa    60
cgttgcttcg gcggtgcgcg ccccccttccc gggggggcgta agccgccggg gaccacaccg   120
aacttcttgt ttttagcgtg tcgtctgagc ttgatacaag caaacctaat ta           172

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide primer.

<400> SEQUENCE: 28
ggaagtaaaa gtcgtaacaa gg                                         22

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide primer.

<400> SEQUENCE: 29
gctgcgttct tcatcgatgc                                            20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide primer.

<400> SEQUENCE: 30
tcctccgctt attgatatgc                                            20

<210> SEQ ID NO 31
<211> LENGTH: 19
<212> TYPE: DNA
<213> ORGANISM: Artificial Sequence
<220> FEATURE:
<223> OTHER INFORMATION: Oligonucleotide primer.

<400> SEQUENCE: 31
tccgtaggtg aacctgcgg                                             19

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide primer.

<400> SEQUENCE: 32
gcatcgatga agaacgcagc                                            20

<210> SEQ ID NO 33

-continued

```
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 33
caggtctgcc cctggcag                                                 18

<210> SEQ ID NO 34
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 34
gtctgcccct ggcaggcc                                                 18

<210> SEQ ID NO 35
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 35
tgcccctggc aggcctaa                                                 18

<210> SEQ ID NO 36
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 36
accgaacctt cttgttta                                                 18

<210> SEQ ID NO 37
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 37
gaaccttctt gtttaagc                                                 18

<210> SEQ ID NO 38
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 38
ccttcttgtt taagcctg                                                 18

<210> SEQ ID NO 39
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 39
```
tcttgtttaa gcctgttg                                        18

<210> SEQ ID NO 40
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 40
tgtttaagcc tgttgtct                                        18

<210> SEQ ID NO 41
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 41
ttaagcctgt tgtctgag                                        18

<210> SEQ ID NO 42
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 42
agcctgttgt ctgagctt                                        18

<210> SEQ ID NO 43
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 43
ctgttgtctg agcttgat                                        18

<210> SEQ ID NO 44
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 44
ttgtctgagc ttgatagc                                        18

<210> SEQ ID NO 45
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 45
tctgagcttg atagcaaa                                        18

<210> SEQ ID NO 46
<211> LENGTH: 18
<212> TYPE: DNA

```
<213> ORGANISM: Artificial Sequence
<220> FEATURE:
<223> OTHER INFORMATION: Oligonucleotide primer/probe.

<400> SEQUENCE: 46
gagcttgata gcaaatct                                                     18

<210> SEQ ID NO 47
<211> LENGTH: 19
<212> TYPE: DNA
<213> ORGANISM: Artificial Sequence
<220> FEATURE:
<223> OTHER INFORMATION: Oligonucleotide primer/probe.

<400> SEQUENCE: 47
cttgatagca aatctatta                                                    19

<210> SEQ ID NO 48
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 48
ttgtttaagc ctgttgtc                                                     18

<210> SEQ ID NO 49
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 49
tttaagcctg ttgtctga                                                     18

<210> SEQ ID NO 50
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 50
tttcatgcct gagagtga                                                     18

<210> SEQ ID NO 51
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 51
catgcctgag agtgatgc                                                     18

<210> SEQ ID NO 52
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 52
gcctgagagt gatgcagt                                                     18
```

<210> SEQ ID NO 53
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 53
tgagagtgat gcagtctg                                                 18

<210> SEQ ID NO 54
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 54
gagtgatgca gtctgagc                                                 18

<210> SEQ ID NO 55
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 55
tgatgcagtc tgagcctg                                                 18

<210> SEQ ID NO 56
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 56
tgcagtctga gcctgaat                                                 18

<210> SEQ ID NO 57
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 57
agtctgagcc tgaataca                                                 18

<210> SEQ ID NO 58
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 58
ctgagcctga atacaaat                                                 18

<210> SEQ ID NO 59
<211> LENGTH: 18
<212> TYPE: DNA
<213> ORGANISM: Artificial Sequence
<220> FEATURE:

<223> OTHER INFORMATION: Oligonucleotide primer/probe.

<400> SEQUENCE: 59
agcctgaata caaatcag                                                 18

<210> SEQ ID NO 60
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 60
ctgaatacaa atcagtca                                                 18

<210> SEQ ID NO 61
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 61
ctgtctttag tgttgtct                                                 18

<210> SEQ ID NO 62
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 62
tctttagtgt tgtctgag                                                 18

<210> SEQ ID NO 63
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 63
ttagtgttgt ctgagctt                                                 18

<210> SEQ ID NO 64
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 64
gtgttgtctg agcttgat                                                 18

<210> SEQ ID NO 65
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 65
ttgtctgagc ttgatagc                                                 18

-continued

```
<210> SEQ ID NO 66
<211> LENGTH: 18
<212> TYPE: DNA
<213> ORGANISM: Artificial Sequence
<220> FEATURE:
<223> OTHER INFORMATION: Oligonucleotide primer/probe.

<400> SEQUENCE: 66
gagcttgata gcaaacct                                                18

<210> SEQ ID NO 67
<211> LENGTH: 19
<212> TYPE: DNA
<213> ORGANISM: Artificial Sequence
<220> FEATURE:
<223> OTHER INFORMATION: Oligonucleotide primer/probe.

<400> SEQUENCE: 67
cttgatagca aacctatta                                               19
```

MOLECULAR IDENTIFICATION OF *ASPERGILLUS* SPECIES

PRIORITY CLAIM

This is a divisional of U.S. patent application Ser. No. 10/514,861, U.S. Pat. No. 7,384,741 filed Nov. 16, 2004, which is the §371 U.S. national stage of PCT Application No. PCT/US03/016076, filed May 16, 2003, which was published in English under PCT Article 21(2), which in turn claims the benefit of U.S. Provisional Patent Application No. 60/381,463, filed May 17, 2002. U.S. patent application Ser. No. 10/514,861 is incorporated by reference herein in its entirety.

FIELD

This invention relates to methods for the detection and species identification of *Aspergillus*, and specifically to the use of internal transcribed spacer 1 (ITS1) nucleic acid sequences to identify or detect an *Aspergillus* species or strain of a species.

BACKGROUND

Improvements in the management and treatment of debilitated medical and surgical patients have been accompanied by an unfortunate increase in the number of life-threatening infections due to pathogenic and opportunistic fungi (McNeil et al., *Clin. Infect. Dis.* 33:641-47, 2001). AIDS, cancer chemotherapy and high dose corticosteroid treatment have all contributed to the increasing number of immunocompromised individuals. Many immunocompromised subjects develop opportunistic infections with saprophytic filamentous fungi, such as *Aspergillus* species, which are found in the environment and were originally considered to be of low virulence (Latge, *Clin. Microbiol. Rev.* 12:310-50, 1999). These infections are often fulminant and fatal in immunocompromised patients. For example, pulmonary and cerebral aspergillosis have mortality rates of 86 and 99%, respectively, even when adequately treated (Denning, *Clin. Infect. Dis.* 23:608-14, 1996).

The advent of new, specific antifungal drugs and treatment regimes has improved the prospects for management of aspergillosis. However, diagnosis remains difficult, and early initiation of appropriate antifungal therapy is critical in reducing mortality rates in immunocompromised patients (Einsele et al., *J. Clin. Microbiol.* 35:1353-60, 1997). Hence rapid diagnostic assays are needed to improve treatment outcomes.

*Aspergillus* is one of the primary pathogens which cause systemic fungal infection treated in hospitals. It usually affects subjects who have had organ transplants, acute leukemias and burns, and can be rapidly fatal if not diagnosed quickly. There are over 150 species of *Aspergillus* present in the soil, air and water, hence accurate detection of important species of *Aspergillus* is often complex and difficult.

Diagnosis of fungal infections is typically made by isolation of the infecting organism in culture, by serologic assays, or through histopathologic examination of tissue (Hamilton, *Med. Mycol.* 36:351-64, 1998). Isolation of *Aspergillus* species in culture can require several days for adequate growth and sporulation to occur, delaying appropriate drug therapy, and a positive culture may represent benign colonization rather than true invasion or infection (de Repentigny, *Clin. Infect. Dis.* 14:S11-22, 1992). When histopathology is performed on tissue sections, the morphological similarities of the various *Aspergillus* species can make definitive species identification difficult.

Alternatively, serological tests can be used to diagnose fungal infections, but most such tests lack the desired sensitivity and/or specificity for a confident diagnosis. Serologic tests on a single serum sample to detect circulating fungal antigens may be inconclusive, and antibody production in the immunocompromised patient population most at risk for invasive aspergillosis is often variable and an unreliable diagnostic indicator (Morrison and Lindsley, *Fungal Pathogenesis: Principles and Practice*, Marcel Dekker, Inc., 667-716, 2001).

Current serological assays do not identify *Aspergillus* to the species level, and are both time-consuming and expensive. In addition, *Aspergillus terreus* has been shown to be resistant to amphotericin B, the most commonly prescribed drug for treating invasive aspergillosis. *Aspergillus fumigatus* has been reported to develop resistance to itraconazole. Thus, there remains a need for a rapid test to identify aspergilli to the species level, to help assist in the selection of appropriate drugs for the treatment of clinical *Aspergillus* infections. Fungal species identification may also be important for detecting organisms in the environment that may be potentially pathogenic, for example to an immunocompromised person who is exposed to that environment.

PCR-based methods of detection, which show promise as rapid techniques to diagnose infections, have been used in the identification of DNA from *Candida* and *Aspergillus* species. However, most of these tests are only genus specific, and are unable to specifically identify many clinically and environmentally important *Aspergillus* species.

Unique internal transcribed sequence 2 (ITS2) coding regions have been used to develop nucleic acid probes for several different species of *Aspergillus* (*A. flavus, A. fumigatus, A. niger, A. terreus*, and *A. nidulans*), as disclosed in U.S. Pat. No. 6,372,430, which is incorporated by reference.

SUMMARY

A novel approach to species identification of a fungus is disclosed herein. In one embodiment, the method takes advantage of the finding that the ITS1 of fungal ribosomal DNA is not well conserved across these species. The present inventors have found that different species of *Aspergillus* have much higher non-conserved regions of the rDNA ITS1 nucleic acid sequence than of the rDNA ITS2 region that has been used for species identification in the past. This surprising finding has permitted the development of a much more specific method of detecting different species of *Aspergillus*, by taking advantage of these sequence differences in ITS1. Particular *Aspergillus* species that can be detected with this method include, but are not limited to, *A. clavatus, A. granulosus, A. sydowii, A. flavipes, A. restrictus, A. versicolor, A. wentii, A. chevalieri*, and *A. ustus*, or any combination or sub-set of these species (such as *A. granulosus, A. clavatus*, and *A. sydowii*).

Certain of the sequences disclosed herein are novel sequences. In a particular embodiment, an isolated nucleic acid molecule includes SEQ ID NO: 1 (from *A. clavatus*), SEQ ID NO: 2 and SEQ ID NO: 3 (from *A. granulosus*), and SEQ ID NO: 4, SEQ ID NO: 5, SEQ ID NO: 6, SEQ ID NO: 7, SEQ ID NO: 8 and SEQ ID NO: 9 (from *A. sydowii*), or a nucleotide sequence with at least 75% (for example at least 85% or at least 95%) sequence identity to the nucleotide sequence of SEQ ID NO: 1 (from *A. clavatus*), SEQ ID NO: 2 and SEQ ID NO: 3 (from *A. granulosus*), and SEQ ID NO: 4, SEQ ID NO: 5, SEQ ID NO: 6, SEQ ID NO: 7, SEQ ID NO: 8 and SEQ ID NO: 9 (from *A. sydowii*), wherein the nucleotide sequence is from a member of the genus *Aspergillus*, such as *clavatus*, *granulosus*, or *sydowii* species.

In another embodiment, an isolated nucleic acid molecule includes a nucleotide sequence set forth as SEQ ID NO: 10, 11 or 12 (from *A. flavipes*) or a degenerate variant thereof, SEQ ID NO: 13 or 14 (from *A. restrictus*) or a 10 degenerate variant thereof, SEQ ID NO: 15, 16, 17 or 18 (from *A. versicolor*) or a degenerate variant thereof, or SEQ ID NO: 19 (from *A. wentii*) or a degenerate variant thereof, wherein the nucleotide sequence identifies a member of the genus *Aspergillus* as a member of *flavipes, restrictus, versicolor*, or *wentii* species.

In yet another embodiment, an isolated nucleic acid molecule includes a nucleotide sequence selected from the group consisting of at least 15 consecutive nucleotides of a nucleotide sequence with at least 75% (for example at least 85% or at least 95%) sequence identity to the nucleic acid sequence shown in SEQ ID NO: 1, at least 15 consecutive nucleotides of a nucleotide sequence with at least 75% (for example at least 85% or at least 95%) sequence identity to the nucleic acid sequence shown in SEQ ID NO: 2 or 3, and at least 15 consecutive nucleotides of a nucleotide sequence with at least 75% (for example at least 85% or at least 95%) sequence identity to the nucleic acid sequence shown in SEQ ID NO: 4, 5, 6, 7, 8 or 9.

In one embodiment, an isolated nucleic acid molecule includes a nucleotide sequence selected from the group consisting of at least 15 consecutive nucleotides of the nucleic acid sequence shown in SEQ ID NO: 10, 11 or 12 or a degenerate variant thereof, at least 15 consecutive nucleotides of the nucleic acid sequence shown in SEQ ID NO: 13 or 14 or a degenerate variant thereof, and at least 15 consecutive nucleotides of the nucleic acid sequence shown in SEQ ID NO: 15, 16, 17 or 18 or a degenerate variant thereof.

In a further embodiment, a method is disclosed for detecting the presence of an *Aspergillus* species in a biological sample, for example by distinguishing one species from another by detecting differences in the ITS1 region of the fungal rRNA. Since it has now been found that the ITS1 region is particularly poorly conserved across these different species, detection of sequence differences in this region is a particularly sensitive and specific approach to identifying the different species. In particular examples, the method includes detecting differences in two or more (for example at least three or all five) of ITS1-V1, ITS-V2, ITS-V3, ITS-V4, and ITS-V5 nucleic acid sequences of *Aspergillus*. The differences can be detected, for example, by sequencing the two or more nucleic acid sequences, or using nucleic acid probes specific for those sequences. The target sequences may be amplified prior to detecting the distinguishing nucleic acid sequences.

In particular disclosed embodiments, the method distinguishing among *Aspergillus granulosus, ustus, sydowii, versicolor* and *nidulans*, and in addition can be used to distinguish among *Aspergillus clavatus, flavipes, restrictus, wentii*, and *chevalieri*.

Examples of the sequences that distinguish the species are:
(a) SEQ ID NO: 1 or a degenerate variant thereof to identify *Aspergillus clavatus;*
(b) SEQ ID NO: 2, SEQ ID NO: 3 or a degenerate variant thereof to identify *Aspergillus granulosus;*
(c) SEQ ID NO: 4, SEQ ID NO: 5, SEQ ID NO: 6, SEQ ID NO: 7, SEQ ID NO: 8, SEQ ID NO: 9, or a degenerate variant thereof to identify *Aspergillus sydowii*.

The variability of the ITS1 V1-5 regions even permits differentiation among strains of the species. For example, it is possible to distinguish between *Aspergillus granulosus* CBS119.5A and NRRL 250, and among *Aspergillus sydowi* iNRRL, CUH1, CUH2, CUH7 and CUH8.

Other examples of sequences that differentiate the species by distinguishing the ITS1-V1, ITS-V2, ITS-V3, ITS-V4, and ITS-V5 nucleotide sequences are
(a) SEQ ID NO: 10, SEQ ID NO: 11, SEQ ID NO: 12 or a degenerate variant thereof to identify *A. flavipes;*
(b) SEQ ID NO: 13, SEQ ID NO: 14 or a degenerate variant thereof to identify *A. restrictus*
(c) SEQ ID NO: 15, SEQ ID NO: 16, SEQ ID NO: 17, SEQ ID NO: 18 or a degenerate variant thereof to identify *A. versicolor;*
(d) SEQ ID NO: 19 or a degenerate variant thereof to identify *A. wenti*.
(e) SEQ ID NO: 20, SEQ ID NO: 21 or a degenerate variant thereof to identify *A. chevalieri*.

In a particular example, the method involves amplifying an *Aspergillus* species ITS1 region including a region having a nucleotide sequence with at least 75% (for example at least 85% or at least 95%) sequence identity to SEQ ID NO: 1, a nucleotide sequence with at least 75% (for example at least 85% or at least 95%) sequence identity to SEQ ID NOs: 2 and 3, and/or a nucleotide sequence with at least 75% sequence identity to SEQ ID NOs: 4-9, and sequencing the ITS1 region, thereby determining the presence of the *Aspergillus* species. Alternatively, the method includes amplifying an *Aspergillus* species ITS1 region selected from the group consisting of SEQ ID NO: 1, SEQ ID NOs: 2 and 3, and/or SEQ ID NOs: 4-9, and sequencing the ITS1 region, thereby determining the presence of the *Aspergillus* species.

In another embodiment, a method is disclosed for detecting the presence of an *Aspergillus* species in a biological sample, by amplifying an *Aspergillus* species ITS1 region selected from the group consisting of SEQ ID NO: 10, 11 and 12 or a degenerate variant thereof, SEQ ID NOs: 13 and 14 or a degenerate variant thereof, SEQ ID NOs: 15-18 or a degenerate variant thereof, SEQ ID NO: 19 or a degenerate variant thereof, and SEQ ID NOs: 20 and 21 or a degenerate variant thereof, and sequencing the ITS1 region, thereby determining the presence of the *Aspergillus* species.

In a further embodiment, a method is disclosed for detecting the presence of an *Aspergillus* species in a biological sample, by amplifying an *Aspergillus* species ITS1 region using oligonucleotide primers comprising at least 15 consecutive nucleotides of an ITS1 region selected from the group consisting of SEQ ID NO: 1, SEQ ID NO: 2 and 3, SEQ ID NO: 4, 5, 6, 7, 8, and 9, SEQ ID NO: 10, 11 and 12, SEQ ID NO: 13 and 14, SEQ ID NO: 15, 16, 17 and 18, SEQ ID NO: 19, and SEQ ID NO: 20 and 21, and sequencing the ITS1 region, thereby determining the presence of the *Aspergillus* species.

In yet a further embodiment, a method is disclosed for detecting the presence of an *Aspergillus* species in a biological sample, by amplifying an *Aspergillus* species ITS1 region using universal fungal primers ITS5 (SEQ ID NO: 28), ITS1 (SEQ ID NO: 31), ITS2 (SEQ ID NO: 29), and ITS4 (SEQ ID NO: 30), followed by hybridization with oligonucleotide probes comprising at least 15 consecutive nucleotides of an ITS1 region selected from the group consisting of SEQ ID NO: 1, SEQ ID NO: 2 and 3, SEQ ID NO: 4, 5, 6, 7, 8 and 9, SEQ ID NO: 10, 11 and 12, SEQ ID NO: 13 and 14, SEQ ID NO: 15, 16, 17, 18, SEQ ID NO: 19, and SEQ ID NO: 20 and 21, with detection of hybridization indicating the presence of the *Aspergillus* species.

Kits for carrying out these methods are also disclosed.

These and other embodiments are disclosed in the detailed description of this specification. Other features and advan-

BRIEF DESCRIPTION OF THE FIGURES

FIG. 2 is an alignment of ITS1 sequences of representative *Aspergillus* species and strains. Dots symbolize identical nucleotides compared to the *A. niger* I sequence; dashes indicate alignment gaps. Aligned sequences are separated by horizontal lines according to their phylogenetic relationship (Samson and Pitt (eds.), *Integration of Modern Taxonomic Methods for Penicillium and Aspergillus Classification*, Harwood Academic Publishers, 2000) and represent the following strains: *A. niger* I (ATCC 1015, ATCC 64028), *A. niger* II (ATCC 16404), *A. flavus* (ATCC 11497, ATCC 34896, ATCC 44310, ATCC 64025), *A. parasiticus* (ATCC 56775), *A. tamarii* (ATCC 64841), *A. flavipes* I (ATCC 11013), *A. flavipes* II (ATCC 16805), *A. flavipes* III (ATCC 24487), *A. candidus* (NRRL 303, NRRL 312), *A. terreus* (ATCC 1012, ATCC 10029, ATCC 7860), *A. chevalieri* (ATCC 16443, ATCC 24546), *A. restrictus* (NRRL 148, NRRL 151), *A. fumigatus* (ATCC 16903, CDC 2570), *A. granulosus* (CBS 119.5A, NRRL 1932), *A. ustus* I (ATCC 14417), *A. ustus* II (ATCC 16801), *A. ustus* III (CUH4), *A. ustus* IV (NRRL 275), *A. ustus* V (NRRL 5077, CUH5), *A. sydowii* I (NRRL 250, NRRL 4768, CUH1, CUH2, CUH8), *A. sydowii* II (CUH7), *A. versicolor* I (ATCC 10072, NRRL 238, NRRL 239), *A. versicolor* II (CUH3), *A. nidulans* I (ATCC 16855, ATCC 64027), and *A. nidulans* II (CDC 040487).

SEQUENCE LISTING

Figure 1:
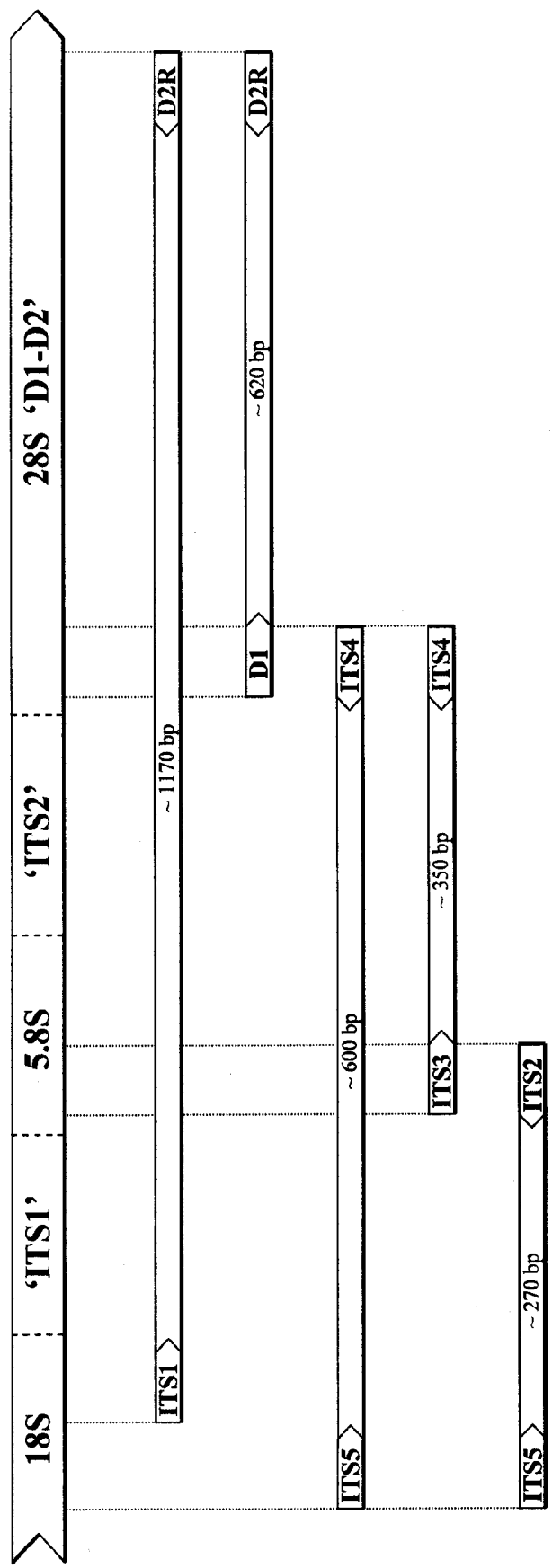
FIG. 1 is a diagram of fungal rDNA. Hybridization sites for the ITS5 and ITS1 amplification primers are shown in the phylogenetically conserved 18S region, hybridization sites for the ITS2 and ITS3 amplification primers are shown in the phylogenetically conserved 5.8S region, and the hybridization site for the ITS4 amplification primer is shown in the phylogenetically conserved 28S region. Arrows designate the direction of amplification.

The nucleic sequences listed in the accompanying sequence listing are shown using standard letter abbreviations for nucleotide bases, as defined in 37 C.F.R. 1.822. Only one strand of each nucleic acid sequence is shown, but the complementary strand and the corresponding RNA sequences of both strands are understood to be included by any reference to the displayed strand.

SEQ ID NO: 1 shows the nucleic acid sequence of the ITS1 region of *A. clavatus* (strain ATCC 9192).

SEQ ID NO: 2 shows the nucleic acid sequence of the ITS1 region of *A. granulosus* (strain CBS119.5A).

SEQ ID NO: 3 shows the nucleic acid sequence of the ITS1 region of *A. granulosus* (strain NRRL 1932).

SEQ ID NO: 4 shows the nucleic acid sequence of the ITS1 region of *A. sydowii* (strain NRRL 250).

SEQ ID NO: 5 shows the nucleic acid sequence of the ITS1 region of *A. sydowii* (strain NRRL 4768).

SEQ ID NO: 6 shows the nucleic acid sequence of the ITS1 region of *A. sydowii* (strain CUH1).

SEQ ID NO: 7 shows the nucleic acid sequence of the ITS1 region of *A. sydowii* (strain CUH2).

SEQ ID NO: 8 shows the nucleic acid sequence of the ITS1 region of *A. sydowii* (strain CUH7).

SEQ ID NO: 9 shows the nucleic acid sequence of the ITS1 region of *A. sydowii* (strain CUH8).

SEQ ID NO: 10 shows the nucleic acid sequence of the ITS1 region of *A. flavipes* (strain ATCC 11013).

SEQ ID NO: 11 shows the nucleic acid sequence of the ITS1 region of *A. flavipes* (strain ATCC 16805).

SEQ ID NO: 12 shows the nucleic acid sequence of the ITS1 region of *A. flavipes* (strain ATCC 24487).

SEQ ID NO: 13 shows the nucleic acid sequence of the ITS1 region of *A. restrictus* (strain NRRL 148).

SEQ ID NO: 14 shows the nucleic acid sequence of the ITS1 region of *A. restrictus* (strain NRRL 151).

SEQ ID NO: 15 shows the nucleic acid sequence of the ITS1 region of *A. versicolor* (strain ATCC 10072).

SEQ ID NO: 16 shows the nucleic acid sequence of the ITS1 region of *A. versicolor* (strain NRRL 238).

SEQ ID NO: 17 shows the nucleic acid sequence of the ITS1 region of *A. versicolor* (strain NRRL 239).

SEQ ID NO: 18 shows the nucleic acid sequence of the ITS1 region of *A. versicolor* (strain CUH3).

SEQ ID NO: 19 shows the nucleic acid sequence of the ITS1 region of *A. wentii* (strain 3650).

SEQ ID NO: 20 shows the nucleic acid sequence of the ITS1 region of *A. chevalieri* (strain ATCC 16443).

SEQ ID NO: 21 shows the nucleic acid sequence of the ITS1 region of *A. chevalieri* (strain ATCC 24546).

SEQ ID NO: 22 shows the nucleic acid sequence of the ITS1 region of *A. ustus* (strain ATCC 14417).

SEQ ID NO: 23 shows the nucleic acid sequence of the ITS1 region of *A. ustus* (strain ATCC 16801).

SEQ ID NO: 24 shows the nucleic acid sequence of the ITS1 region of *A. ustus* (strain NRRL 275).

SEQ ID NO: 25 shows the nucleic acid sequence of the ITS1 region of *A. ustus* (strain NRRL 5077).

SEQ ID NO: 26 shows the nucleic acid sequence of the ITS1 region of *A. ustus* (strain CUH4).

SEQ ID NO: 27 shows the nucleic acid sequence of the ITS1 region of *A. ustus* (strain CUH5).

SEQ ID NO: 28 shows the nucleic acid sequence of fungal universal forward primer ITS5.

SEQ ID NO: 29 shows the nucleic acid sequence of fungal universal reverse primer ITS2.

SEQ ID NO: 30 shows the nucleic acid sequence of fungal universal reverse primer ITS4.

SEQ ID NO: 31 shows the nucleic acid sequence of fungal universal forward primer ITS1.

SEQ ID NO: 32 shows the nucleic acid sequence of fungal universal forward primer ITS3.

SEQ ID NO: 33 shows the nucleic acid sequence of an exemplary *A. granulosus* ITS1 primer/probe.

SEQ ID NO: 34 shows the nucleic acid sequence of an exemplary *A. granulosus* ITS1 primer/probe.

SEQ ID NO: 35 shows the nucleic acid sequence of an exemplary *A. granulosus* ITS1 primer/probe.

SEQ ID NO: 36 shows the nucleic acid sequence of an exemplary *A. granulosus* ITS1 primer/probe.

SEQ ID NO: 37 shows the nucleic acid sequence of an exemplary *A. granulosus* ITS1 primer/probe.

SEQ ID NO: 38 shows the nucleic acid sequence of an exemplary *A. granulosus* ITS1 primer/probe.

SEQ ID NO: 39 shows the nucleic acid sequence of an exemplary *A. granulosus* ITS1 primer/probe.

SEQ ID NO: 40 shows the nucleic acid sequence of an exemplary *A. granulosus* ITS1 primer/probe.

SEQ ID NO: 41 shows the nucleic acid sequence of an exemplary *A. granulosus* ITS1 primer/probe.

SEQ ID NO: 42 shows the nucleic acid sequence of an exemplary *A. granulosus* ITS1 primer/probe.

SEQ ID NO: 43 shows the nucleic acid sequence of an exemplary *A. granulosus* ITS1 primer/probe.

SEQ ID NO: 44 shows the nucleic acid sequence of an exemplary *A. granulosus* ITS1 primer/probe.

SEQ ID NO: 45 shows the nucleic acid sequence of an exemplary *A. granulosus* ITS1 primer/probe.

SEQ ID NO: 46 shows the nucleic acid sequence of an exemplary *A. granulosus* ITS1 primer/probe.

SEQ ID NO: 47 shows the nucleic acid sequence of an exemplary *A. granulosus* ITS1 primer/probe.

SEQ ID NO: 48 shows the nucleic acid sequence of an exemplary *A. granulosus* ITS1 primer/probe.

SEQ ID NO: 49 shows the nucleic acid sequence of an exemplary *A. granulosus* ITS1 primer/probe.

SEQ ID NO: 50 shows the nucleic acid sequence of an exemplary *A. nidulans* ITS1 primer/probe.

SEQ ID NO: 51 shows the nucleic acid sequence of an exemplary *A. nidulans* ITS1 primer/probe.

SEQ ID NO: 52 shows the nucleic acid sequence of an exemplary *A. nidulans* ITS1 primer/probe.

SEQ ID NO: 53 shows the nucleic acid sequence of an exemplary *A. nidulans* ITS1 primer/probe.

SEQ ID NO: 54 shows the nucleic acid sequence of an exemplary *A. nidulans* ITS1 primer/probe.

SEQ ID NO: 55 shows the nucleic acid sequence of an exemplary *A. nidulans* ITS1 primer/probe.

SEQ ID NO: 56 shows the nucleic acid sequence of an exemplary *A. nidulans* ITS1 primer/probe.

SEQ ID NO: 57 shows the nucleic acid sequence of an exemplary *A. nidulans* ITS1 primer/probe.

SEQ ID NO: 58 shows the nucleic acid sequence of an exemplary *A. nidulans* ITS1 primer/probe.

SEQ ID NO: 59 shows the nucleic acid sequence of an exemplary *A. nidulans* ITS1 primer/probe.

SEQ ID NO: 60 shows the nucleic acid sequence of an exemplary *A. nidulans* ITS1 primer/probe.

SEQ ID NO: 61 shows the nucleic acid sequence of an exemplary *A. ustus* ITS1 primer/probe.

SEQ ID NO: 62 shows the nucleic acid sequence of an exemplary *A. ustus* ITS1 primer/probe.

SEQ ID NO: 63 shows the nucleic acid sequence of an exemplary *A. ustus* ITS1 primer/probe.

SEQ ID NO: 64 shows the nucleic acid sequence of an exemplary *A. ustus* ITS1 primer/probe.

SEQ ID NO: 65 shows the nucleic acid sequence of an exemplary *A. ustus* ITS1 primer/probe.

SEQ ID NO: 66 shows the nucleic acid sequence of an exemplary *A. ustus* ITS1 primer/probe.

SEQ ID NO: 67 shows the nucleic acid sequence of an exemplary *A. ustus* ITS1 primer/probe.

DETAILED DESCRIPTION

I. Explanation of Terms

Unless otherwise noted, technical terms are used according to conventional usage. Definitions of common terms in molecular biology may be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995.

As used herein, the singular forms "a," "an," and "the," refer to both the singular as well as plural, unless the context clearly indicates otherwise. Similarly, the word "or" is intended to include "and" unless the context clearly indicates otherwise. Also, as used herein, the term "comprises" means "includes." Hence "comprising A or B" means including A, B, or A and B. In addition, the materials, methods, and examples are illustrative only and not intended to be limiting.

In order to facilitate review of the various embodiments of the invention, the following explanations of specific terms are provided:

Amplification: of a nucleic acid molecule (e.g., a DNA or RNA molecule) refers to use of a technique that increases the number of copies of a nucleic acid molecule in a sample. An example of amplification is polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques.

The PCR method can be modified in certain embodiments. For example, a polymerase chain reaction-enzyme immunoassay (PCR-EIA) method can be used for amplification and differentiation of fungi. The PCR-EIA method is described in Elie et al., *J. Clin. Microbiol.* 36:3260-65, 1998, and can be modified to suit particular embodiments.

Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320, 308; gap filling ligase chain reaction amplification, as disclosed in U.S. Pat. No. 5,427,930; and NASBA RNA transcription-free amplification, as disclosed in U.S. Pat. No. 6,025,134.

Animal: A living multi-cellular vertebrate or invertebrate organism, a category that includes, for example, mammals and birds. The term mammal includes both human and non-human mammals. Similarly, the term "subject" includes both human and veterinary subjects.

cDNA (complementary DNA): A piece of DNA lacking internal, non-coding segments (introns) and transcriptional regulatory sequences. cDNA also may contain untranslated regions (UTRs) that are responsible for translational control in the corresponding RNA molecule. cDNA is synthesized in the laboratory by reverse transcription from messenger RNA extracted from cells.

Degenerate variant: A "degenerate variant" of a probe or primer includes sequences that have altered nucleic acid sequences, but retain their ability to bind to the target sequences (and identify or amplify the fungal target) with sufficient specificity. In some particular examples, no more than about 1, 2, 5, or 10 nucleic acids are changed, or the probe or primer retains at least 80%, 85%, 90%, or 95% sequence identity to the original sequence. Degenerate variants also include probe or primer sequences to which additional sequence has been added, while still retaining the noted specificity of the probe or primer.

A "degenerate variant" or "minor variant" of an *Aspergillus* ITS I sequence includes sequences that have altered nucleic acid sequences, but retain their ability to identify particular *Aspergillus* species. In some particular examples, no more than about 1, 2, 5, or 10 nucleic acids are changed.

Fungus: Living, single-celled and multicellular organisms belonging to the kingdom Fungi. Most species are characterized by a lack of chlorophyll and presence of chitinous cell walls, and some fungi may be multinucleated. In one embodiment, a fungus is an *Aspergillus* species. Representative, non-limiting examples of *Aspergillus* include the species listed in Table I below, such as *A. chevalieri, A. clavatus, A. flavipes, A. granulosus, A. restrictus, A. sydowii, A. ustus, A. versicolor*, and *A. wentii*.

Homolog: A nucleotide sequence that shares a common ancestor with another nucleotide sequence; the homologs diverged when a species carrying that ancestral sequence split into two species.

Isolated: An "isolated" microorganism (such as a fungus) has been substantially separated or purified away from microorganisms of different types, strains, or species. For example, a colony of *Aspergillus* clavatus would be considered an "isolated" *Aspergillus clavatus*. Microorganisms can be isolated by a variety of techniques, including serial dilution and culturing.

An "isolated" biological component (such as a nucleic acid molecule or protein) has been substantially separated or purified away from other biological components in the cell of the organism in which the component naturally occurs. The term "isolated" does not require absolute purity. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

ITS1: The first internal transcribed spacer sequence of fungal rDNA. As illustrated in FIG. 1, a diagram of the fungal rDNA region, the ITS1 sequence is located between the 18S and 5.8S coding sequences. The ITS1 region varies from approximately 142 to 187 nucleotides in length depending upon the species examined. In one embodiment, the nucleotides in the ITS1 sequence can be numbered beginning with the first nucleotide downstream of the 18S coding sequence and ending with the last nucleotide directly in advance of the 5.8S coding sequence.

The hypervariable regions of ITS1 are defined as follows with reference to FIG. 2: ITS1-V1, position 8-30 (12-21 nucleotides in length); ITS1-V2, position 50-67 (13-14 nucleotides in length); ITS1-V3, position 81-141 (12-54 nucleotides in length); ITS1-V4, position 151-181 (23-28 nucleotides in length); and ITS1-V5, position 192-215 (17-21 nucleotides in length). Compared to the ITS1-V3 sequence of *A. niger* (54 nucleotides), notably shorter corresponding sequences were found for *A. chevalieri* (12 nucleotides), *A. granulosus* (21 nucleotides), *A. ustus* (21-30 nucleotides), *A. sydowii* (22 nucleotides), *A. versicolor* (22 nucleotides), and *A. nidulans* (21-22 nucleotides).

Oligonucleotide: A linear polynucleotide sequence of between 5 and 100 nucleotide bases in length.

Operably linked: A first molecule, such as a nucleic acid or protein, is operably linked with a second molecule when the first molecule is placed in a functional relationship with the second molecule. For instance, a promoter is operably linked to a nucleic acid coding sequence if the promoter affects the transcription or expression of the coding sequence. Additionally, an intron is operably linked to an exon for the function of splicing. Generally, operably linked nucleotide sequences are contiguous and, where necessary to join two protein-coding regions, in the same reading frame.

ORF (open reading frame): A series of nucleotide triplets (codons) coding for amino acids without any internal termination codons. These sequences are usually translatable into a peptide.

Probes and primers: Nucleic acid probes and primers can be readily prepared based on the nucleic acid molecules provided in this invention, and therefore provide a substantial utility for the disclosed sequences. A probe comprises an isolated nucleic acid capable of hybridizing to a template nucleic acid, and a detectable label or reporter molecule can be attached to a probe. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed in, for example, Sambrook et al., *Molecular Cloning: A Laboratory Manual*, Cold Spring Harbor Laboratory Press, 2001; and Ausubel et al. (eds.), *Short Protocols in Molecular Biology*, John Wiley and Sons, 1999.

Primers are short nucleic acid molecules, for example DNA oligonucleotides nucleotides or more in length. Primers can be annealed to a complementary target DNA strand by nucleic acid hybridization to form a hybrid between the primer and the target DNA strand, and the primer can be extended along the target DNA strand by a DNA polymerase enzyme. Primer pairs can be used for amplification of a nucleic acid sequence, e.g., by PCR or other nucleic acid amplification methods.

Methods for preparing and using probes and primers are described, for example, in Sambrook et al.; Ausubel et al. (eds.); and Innis et al., *PCR Applications, Protocols for Functional Genomics*, Academic Press, Inc., 1999. PCR primer pairs can be derived from a known sequence, for example, by using computer programs intended for that purpose such as Primer3, Whitehead Institute for Biomedical Research, Cambridge, Mass.; the program is accessible through the Whitehead Institute's website.

The specificity of a particular probe or primer increases with its length. Thus, as one non-limiting example, a primer comprising 15 consecutive nucleotides of the *A. clavatus ITS*1 sequence will anneal to a target sequence, such as another ITS1 homolog from the family contained within an *A. clavatus* genomic DNA library, with a higher specificity than a corresponding primer of only 10 nucleotides. Thus, in order to obtain greater specificity, probes and primers can be selected that comprise 20, 25, 30, 35, 40, 50, 75, 100, or more consecutive nucleotides of *A. clavatus* ITS1 sequence. The present disclosure thus includes isolated nucleic acid molecules (probes and primers) that comprise specified lengths of a fungal ITS1 sequence. Such molecules can comprise at least 10, 20, 25, 30, 35, 40, 50, 75, or 100 consecutive nucleotides of the ITS1 sequence, and can be obtained from any region of the ITS1 sequence.

Any of the probes or primers disclosed herein can also be of a maximum length, for example no more than 15, 25, 25, 40, 50, 75 or 100 nucleotides in length.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sample: Encompasses a sample obtained from an animal, plant, or the environment. An "environmental sample" includes a sample obtained from inanimate objects or reservoirs within an indoor or outdoor environment, including, but not limited to: soil, water, dust, and air samples.

Biological sample: A sample obtained from a plant or animal subject. As used herein, biological samples include all clinical samples useful for detection of fungal infection in subjects, including, but not limited to, cells, tissues, and bodily fluids, such as blood, derivatives and fractions of blood (such as serum); biopsied or surgically removed tissue, including tissues that are unfixed, frozen, or fixed in formalin or paraffin; tears; milk; skin scrapes; surface washings; urine; sputum; cerebrospinal fluid; prostate fluid; pus; bone marrow aspirates; bronchoalveolar levage (BAL); and saliva. In particular embodiments, the biological sample is obtained from an animal subject, such as blood, serum, cerebrospinal fluid, BAL, pus, or a skin lesion.

Sequence identity: The similarity between two nucleic acid sequences, is expressed in terms of the similarity between the sequences, otherwise referred to as sequence identity. Sequence identity is frequently measured in terms of percentage identity, similarity, or homology; a higher percentage identity indicates a higher degree of sequence similarity. Homologs of fungal ITS1 sequences will possess a relatively high degree of sequence identity when aligned using standard methods.

The NCBI Basic Local Alignment Search Tool (BLAST), Altschul et al., *J. Mol. Biol.* 215:403-10, 1990, is available from several sources, including the National Center for Biotechnology Information (NCBI, Bethesda, Md.), for use in connection with the sequence analysis programs blastp, blastn, blastx, tblastn and tblastx. It can be accessed through the NCBI website. A description of how to determine sequence identity using this program is also available on the website.

When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described on the NCBI website.

These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al.; and Tijssen, *Hybridization With Nucleic Acid Probes, Part I: Theory and Nucleic Acid Preparation*, Laboratory Techniques in Biochemistry and Molecular Biology, Elsevier Science Ltd., 1993. Nucleic acid molecules that hybridize under stringent conditions to a fungal ITS1 sequence will typically hybridize to a probe based on either an entire ITS1 sequence or selected portions of the ITS1 sequence under wash conditions of 2×SSC at 50° C.

Transformed: A transformed cell is a cell into which a nucleic acid has been introduced by molecular biology techniques. The term "transformation" encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector can include nucleic acid sequences that permit it to replicate in a host cell, such as an origin of replication. A vector can also include one or more selectable marker genes and other genetic elements.

This disclosure provides a simple, rapid, and useful method for differentiating species of *Aspergillus* from one another, and from other environmentally, clinically or medically important fungi.

This approach is made possible by providing the ITS1 nucleotide sequences of several clinically important species of *Aspergillus*. Fungal DNA can be amplified using primers, such as universal fungal primers (for example universal primers ITS1, ITS2, ITS3, ITS4, or ITS5). The different species of *Aspergillus* are then differentiated by taking advantage of the ITS1 sequence differences between these species and between different sequevars of a species. For example, the amplified fungal DNA can be sequenced in a high speed sequencer, such that sequence differences between the different *Aspergillus* species are associated with a particular species of *Aspergillus* from which the sequence was obtained.

While the ITS1 sequences of some *Aspergillus* species were previously known, the sequences of many others disclosed herein are novel sequences that were not previously available to distinguish different *Aspergillus* species from one another. The sequences (and the complement) of the sequences claimed in this disclosure, along with any modifications to these sequences, may be utilized in assays for the identification of fungi based on several existing methodologies, as well as future improvements and alterations of this technology. These techniques include, but are not limited to, assays based on hybridization, ligation, polymerization, depolymerization, sequencing, chemical degradation, enzymatic digestion, electrophoresis, chromatography and amplification.

In addition to the 27 different ITS1 sequences (SEQ ID NOs: 1-27) of clinically important *Aspergillus* species and sequevars thereof, also provided are the sequences of several universal fungal primers (SEQ ID NOs: 28-32) that can be used to amplify the *Aspergillus* nucleic acid, prior to species or sequevars identification by the nucleic acid differences disclosed herein.

Those versed in the art will recognize that specification of a single-stranded DNA sequence implies the utility of the complementary DNA sequence, as well as the two equivalent RNA sequences, for detecting species or strain differences. Furthermore, sequences incorporating modifications of any of the moieties comprising the nucleic acid (such as the sugar or the backbone) are functional equivalents of the sequence. These sequences (or subsequences thereof) can themselves serve as probes or primers.

II. *Aspergillus* Sequences

The disclosure provides isolated ITS1 nucleic acid molecules from *Aspergillus* species, which can be used for the detection and species identification of *Aspergillus*. The disclosure encompasses isolated ITS1 nucleic acid molecules from *A. clavatus, A. granulosus, A. sydowii, A. flavipes, A. restrictus, A. versicolor, A. wentii, A. chevalieri,* and *A. ustus*. Specific nucleic acid molecules include:

```
A. clavatus (strain ATCC 9192):
                                       (SEQ ID NO: 1)
CCGAGTGCGGGCCCTCTGGGTCCAACCTCCCACCCGTGTTTATCGTACCT

TGTTGCTTCGGCGGGCCCGCCGTCTTCGGACGGCCGCCGGGGAGGCCTCC
```

-continued

GCGCCCCCGGGCCCGCGCCCGCCGAAGACCACAACATGAACTCTGTTCTG

AAGTTTTGCAGTCTGAGTTGATTATCATAATCAGTTA.

A. granulosus (strain CBS 119.5A):
(SEQ ID NO: 2)
CCGAGTGCAGGTCTGCCCCTGGGCAGGCCTAACCTCCCACCCGTGAATAC

CTGACCAACGTTGCTTCGGCGGTGCGCCCCTCCGGGGGCAGCCGCCGGAG

ACCACACCGAACCTCTTGTTTAAGCCTGTTGTCTGAGCTTGATAGCAAAT

CTATTA.

A. granulosus (strain NRRL 1932):
(SEQ ID NO: 3)
CCGAGTGCAGGTCTGCCCCTGGGCAGGCCTAACCTCCCACCCGTGAATAC

CTGACCAACGTTGCTTCGGCGGTGCGCCCCTCCGGGGGCAGCCGCCGGAG

ACCACACCGAACCTCTTGTTTAAGCCTGTTGTCTGAGCTTGATAGCAAAT

CTATTA.

A. sydowii (strain NRRL 250):
(SEQ ID NO: 4)
CTGAGTGCGGGCTGCCTCCGGGCGCCCAACCTCCCACCCGTGAATACCTA

ACACTGTTGCTTCGGCGGGGAACCCCCTCGGGGGCGAGCCGCCGGGGACT

ACTGAACTTCATGCCTGAGAGTGATGCAGTCTGAGTCTGAATATAAAATC

AGTCA.

A. sydowii (strain NRRL 4768):
(SEQ ID NO: 5)
CTGAGTGCGGGCTGCCTCCGGGCGCCCAACCTCCCACCCGTGAATACCTA

ACACTGTTGCTTCGGCGGGGAACCCCCTCGGGGGCGAGCCGCCGGGGACT

ACTGAACTTCATGCCTGAGAGTGATGCAGTCTGAGTCTGAATATAAAATC

AGTCA.

A. sydowii (strain CUH1):
(SEQ ID NO: 6)
CTGAGTGCGGGCTGCCTCCGGGCGCCCAACCTCCCACCCGTGAATACCTA

ACACTGTTGCTTCGGCGGGGAACCCCCTCGGGGGCGAGCCGCCGGGGACT

ACTGAACTTCATGCCTGAGAGTGATGCAGTCTGAGTCTGAATATAAAATC

AGTCA.

A. sydowii (strain CUH2):
(SEQ ID NO: 7)
CTGAGTGCGGGCTGCCTCCGGGCGCCCAACCTCCCACCCGTGAATACCTA

ACACTGTTGCTTCGGCGGGGAACCCCCTCGGGGGCGAGCCGCCGGGGACT

ACTGAACTTCATGCCTGAGAGTGATGCAGTCTGAGTCTGAATATAAAATC

AGTCA.

A. sydowii (strain CUH7):
(SEQ ID NO: 8)
CTGAGTGCGGGCTGCCTCCGGGCGCCCAACCTCCCACCCGTGAATACCTA

ACACTGTTGCTTCGGCGGGGAGCTCCCTCGGGGGCGAGCCGCCGGGGACT

ACTGAACTTCATGCCTGAGAGTGATGCAGTCTGAGTCTGAATATAAAATC

AGTCA.

A. sydowii (strain CUH8):
(SEQ ID NO: 9)
CTGAGTGCGGGCTGCCTCCGGGCGCCCAACCTCCCACCCGTGAATACCTA

ACACTGTTGCTTCGGCGGGGAACCCCCTCGGGGGCGAGCCGCCGGGGACT

ACTGAACTTCATGCCTGAGAGTGATGCAGTCTGAGTCTGAATATAAAATC

AGTCA.

A. flavipes (strain ATCC 11013):
(SEQ ID NO: 10)
CCGAGTGAGGGTCCTCGTGGCCCAACCTCCCACCCGTGACTACTGTACCA

CTGTTGCTTCGGCGGGCCCGCCAGCGTCCGCTGGCCGCCGGGGGGCTTCT

GCCCCCGGGCCCGTGCCCGCCGGAGACCCCAACACGAACACTGTTTCTGA

AAGCCTGTATGAATTCGATTCTTTGTAATCAGTTA.

A. flavipes (strain ATCC 16805):
(SEQ ID NO: 11)
CCGAGTGAGGGTCCTCGTGGCCCAACCTCCCACCCGTGACTACTGTACCA

CTGTTGCTTCGGCGGGCCCGCCAGCCTAGCTGGCCGCCGGGGGGCTTCTG

CCCCCGGGCCCGCGCCCGCCGGAGACCCCAACACGAACACTGTTTCTGAA

AGCCTGTATGAATCCGATTCTTTGTAATCAGTTA.

A. flavipes (strain ATCC 24487):
(SEQ ID NO: 12)
CCGAGTGAGGGTCCTCGTGGCCCAACCTCCCACCCGTGACTACTGTACCA

CTGTTGCTTCGGCGGGCCCGCCAGCGCCCGCTGGCCGCCGGGGGGCTTCT

GCCCCCGGGCCCGTGCCCGCCGGAGACCCCAACACGAACACTGTTTCTGA

AAGCCTGTATGAATTCGATTCTTTGTAATCAGTTA.

A. restrictus (strain NRRL 148):
(SEQ ID NO: 13)
CCGAGTGCGGGCCCTCTGGGTCCAACCTCCCATCCGTGTCTCTTGTACCC

TGTTGCTTCGGCGGGCCCGCCTTCATGGCCGCCGGGGGGCTTCTGCCCCC

GGGCCCGCGCCCGCCGGAGACTCCAACATTGAACACTGTCTGAAGGTTGC

AGTCTGAGTTTTCATATAAGAAAAATCGTTA.

A. restrictus (strain NRRL 151):
(SEQ ID NO: 14)
CCGAGTGCGGGCCCTCTGGGTCCAACCTCCCATCCGTGTCTCTTGTACCC

TGTTGCTTCGGCGGGCCCGCCTTCATGGCCGCCGGGGGGCTTCTGCCCCC

GGGCCCGCGCCCGCCGGAGACTCCAACATTGAACACTGTCTGAAGGTTGC

AGTCTGAGTTTTCATATAAGAAAAATCGTTA.

A. versicolor (strain ATCC 10072):
(SEQ ID NO: 15)
CTGAGTGCGGGCTGCCTCCGGGCGCCCAACCTCCCACCCGTGACTACCTA

ACACTGTTGCTTCGGCGGGAGCCCTCTCGGGGGCGAGCCGCCGGGGACT

ACTGAACTTCATGCCTGAGAGTGATGCAGTCTGAGTCTGAATATAAAATC

AGTCA.

A. versicolor (strain NRRL 238):
(SEQ ID NO: 16)
CTGAGTGCGGGCTGCCTCCGGGCGCCCAACCTCCCACCCGTGACTACCTA

ACACTGTTGCTTCGGCGGGAGCCCTCTCGGGGGCGAGCCGCCGGGGACT

ACTGAACTTCATGCCTGAGAGTGATGCAGTCTGAGTCTGAATATAAAATC

AGTCA.

A. versicolor (strain NRRL 239):
(SEQ ID NO: 17)
CTGAGTGCGGGCTGCCTCCGGGCGCCCAACCTCCCACCCGTGACTACCTA

ACACTGTTGCTTCGGCGGGAGCCCTCTCGGGGGCGAGCCGCCGGGGACT

-continued

ACTGAACTTCATGCCTGAGAGTGATGCAGTCTGAGTCTGAATATAAAATC

AGTCA.

A. versicolor (strain CUH3):
(SEQ ID NO: 18)
CCGAGTGCGGGCTGCCTCCGGGCGCCCAACCTCCCACCCGTGACTACCTA

ACACTGTTGCTTCGGCGGGGAGCCCTCTCGGGGGCGAGCCGCCGGGGACT

ACTGAACTTCATGCCTGAGAGTGATGCAGTCTGAGTCTGAATATAAAATC

AGTCA.

A. wentii (strain 3650):
(SEQ ID NO: 19)
CCGAGTGAGGACCTAACCGGTCCAACCTCCCACCCGTGTCTATCGTACCT

TGTTGCTTCGGCGGGCCCGCCATTCGTGGCCGCCGGGGGGCATCTCGCCC

CCGGGCCCGCGCCCGCCGGAGACACCAACACGAACACTGTCTGAAGGTTG

CAGTCTGAGTCGATTTATTTAATCGTTA.

A. chevalieri (strain ATCC 16443):
(SEQ ID NO: 20)
CCGAGTGCGGGCCCTCTGGGTCCAACCTCCCATCCGTGTCTATCTGTACC

CTGTTGCTTCGGCGTGGCCACGGCCCGCCGGAGACTAACATTTGAACGCT

GTCTGAAGTTTGCAGTCTGAGTTTTTAGTTAAACAATCGTTA.

A. chevalieri (strain ATCC 24546):
(SEQ ID NO: 21)
CCGAGTGCGGGCCCTCTGGGTCCAACCTCCCATCCGTGTCTATCTGTACC

CTGTTGCTTCGGCGTGGCCACGGCCCGCCGGAGACTAACATTTGAACGCT

GTCTGAAGTTTGCAGTCTGAGTTTTTAGTTAAACAATCGTTA.

A. ustus (strain ATCC 14417):
(SEQ ID NO: 22)
CCGAGTGCAGGTCTGCCCCCGGGCAGGCCTAACCTCCCACCCGTGAATAC

CTGACCAACGTTGCTTCGGCGGTGCGCCCCCCGGGGGTAGCCGCCGGAG

ACCACACCGAACCTCCTGTCTTTAGTGTTGTCTGAGCTTGATAGCAAACC

TATTA.

A. ustus (strain ATCC 16801):
(SEQ ID NO: 23)
CCGAGTGCAGGTCTGCCCCCGGGCAGGCCTAACCTCCCACCCGTGAATAC

CTGACCAACGTTGCTTCGGCGGTGCGCCCCTCCGGGGGTAGCCGCCGGAG

ACCACATTGAACCTCTTGTCTTTAGTGTTGTCTGAGCTTGATAGCAAACC

TATTA.

A. ustus (strain NRRL 275):
(SEQ ID NO: 24)
CCGAGTGCAGGTCTGCCCCCGGGCAGGCCTAACCTCCCACCCGTGAATAC

CTGACCAACGTTGCTTCGGCGGTGCGCTCCCCCGGGGGCAGCCGCCGGA

GACCACACCGAACCTCTTGTTATAGCGTGTCGTCTGAGCTTGATACAAGC

AAACCTAATTA.

A. ustus (strain NRRL 5077):
(SEQ ID NO: 25)
CCGAGTGCAGGCCTCGCCCCACAGGCAGGCCTAACCTCCCACCCGTGAAT

ACCTGACCAACGTTGCTTCGGCGGTGCGCGCCCCTTCCCGGGGGGCGTA

AGCCGCCGGGGACCACACCGAACTTCTTGTTTTTAGCGTGTCGTCTGAGC

TTGATACAAGCAAACCTAATTA.

A. ustus (strain CUH4):
(SEQ ID NO: 26)
CCGAGTGCAGGTCTGCCCCCGGGCAGGCCTAACCTCCCACCCGTGAATAC

CTGACCAACGTTGCTTCGGCGGTGCGCCCCCCCCGGGGGTAGCCGCCGGA

GACCACACCGAACCTCCTGTCTTTAGTGTTGTCTGAGCTTGATAGCAAAC

CTATTA.

A. ustus (strain CUH5):
(SEQ ID NO: 27)
CCGAGTGCAGGCCTCGCCCCACAGGCAGGCCTAACCTCCCACCCGTGAAT

ACCTGACCAACGTTGCTTCGGCGGTGCGCGCCCCCTTCCCGGGGGGCGTA

AGCCGCCGGGGACCACACCGAACTTCTTGTTTTTAGCGTGTCGTCTGAGC

TTGATACAAGCAAACCTAATTA.

In addition, the disclosure encompasses nucleic acid sequences (which as defined herein also includes the complementary sequence and corresponding RNA sequences) with at least 75% (for example at least 85%, 95% or 98%) sequence identity to the isolated ITS1 sequences from *A. clavatus* (SEQ ID NO: 1), *A. granulosus* (SEQ ID NOs: 2 and 3), and *A. sydowii* (SEQ ID NOs: 4-9). The disclosure also encompasses the isolated ITS1 nucleic acid sequences from *A. flavipes* (SEQ ID NOs: 10-12), *A. restrictus* (SEQ ID NOs: 13 and 14), and *A. versicolor* (SEQ ID NOs: 15-18), or degenerate variants thereof. Such sequences can be used as probes or primers for the detection or amplification of target sequences.

Also disclosed are isolated oligonucleotides (which as defined herein also includes the complementary sequence and corresponding RNA sequences) including at least about 10 consecutive nucleotides, or at least about 15, 20 or 25 consecutive nucleotides, from the *Aspergillus* ITS1 sequences disclosed herein, including any nucleic acid sequences having at least 75% (for example at least 85%, 95% or 98%) sequence identity to the isolated ITS1 sequences from *A. clavatus* (SEQ ID NO: 1), *A. granulosus* (SEQ ID NOs: 2 and 3), and *A. sydowii* (SEQ ID NOs: 4-9). Isolated oligonucleotides can be of at least 10 consecutive nucleotides in length, or 15, 20 or 25 consecutive nucleotides in length, or longer. In one embodiment, the oligonucleotides are from *A. flavipes* (SEQ ID NOs: 10-12), *A. restrictus* (SEQ ID NOs: 13 and 14), and *A. versicolor* (SEQ ID NOs: 15-18), or degenerate variants thereof. These oligonucleotides can be employed as effective DNA hybridization probes or primers useful for amplification. Such probes and primers are particularly useful in the detection and speciation of *Aspergillus*.

In some embodiments, any of the probes or primers disclosed herein is also of a maximum length, for example no more than 15, 25, 25, 40, 50, 75, 100, or 150 nucleotides in length.

Also disclosed herein are the isolated ITS1 nucleic acid sequences from *A. ustus* shown in SEQ ID NOs: 22-27.

Any of the isolated nucleic acid sequences disclosed herein may consist or consist essentially of the disclosed sequences, or comprise nucleic acid molecules that have a maximum length of 15, 20, 25, 30, 35, 40, 45, 50, 55, 60, 65, 70, 75 or 80 contiguous nucleotides of the disclosed sequence. The disclosed contiguous sequences may also be joined at either end to other unrelated sequences.

III. Method of Detecting *Aspergillus* ITS1 Sequences

The presence of *Aspergillus* within a sample can be detected using the ITS1 sequences described herein.

Aspergillus DNA can be directly detected or amplified prior to detection and identification of the Aspergillus species from which the DNA originated using these ITS1 sequences. In one embodiment, the species of Aspergillus in a sample is determined by sequence analysis. The methods described herein can be used for any purpose where the detection of Aspergillus is desirable, including diagnostic and prognostic applications, such as in laboratory and clinical settings.

In one embodiment, the detection method includes the step of amplifying with a nucleic acid amplification method an Aspergillus ITS1 sequence in a sample of interest. In one specific embodiment, amplification is by PCR, and the method utilizes two or more oligonucleotide primers from the ITS1 sequences, followed by sequence analysis for identification of the Aspergillus species. In one specific, non-limiting example, PCR is utilized for amplification.

Appropriate samples include any conventional environmental or biological samples, including clinical samples obtained from a human or veterinary subject, for instance blood or blood-fractions (e.g., serum), sputum, saliva, oral or washings, skin scrapes, biopsied tissue (for example bronchoscopy samples), bronchoalveolar lavage (BAL) washings, cerebrospinal fluid, or prostate fluid. Standard techniques for acquisition of such samples are available (see, e.g. Schluger et al., *J. Exp. Med.* 176:1327-33, 1992; Bigby et al., *Am. Rev. Respir. Dis.* 133:515-18, 1986; Kovacs et al., *NEJM* 318:589-93, 1988; and Ognibene et al., *Am. Rev. Respir. Dis.* 129:929-32, 1984). The sample can be used directly or can be processed, such as by adding solvents, preservatives, buffers, or other compounds or substances.

In one embodiment, nucleic acids are isolated from the sample. DNA or RNA can be extracted using standard methods. For instance, rapid DNA preparation can be performed using a commercially available kit (e.g., the Qiagen Tissue Kit, Qiagen, Inc., Valencia, Calif.). The DNA preparation technique can be chosen to yield a nucleotide preparation that is accessible to and amenable to nucleic acid amplification.

In one specific, non-limiting example, universal fungal primers ITS5 (SEQ ID NO: 28), ITS2 (SEQ ID NO: 29), and ITS4 (SEQ ID NO: 30) (see FIG. 1) are used to amplify the identified sequences from *A. clavatus* (SEQ ID NO: 1), *A. granulosus* (SEQ ID NOs: 2 and 3), and *A. sydowii* (SEQ ID NOs: 4-9), or sequences 75%, 85%, 90%, or 95% identical, followed by sequence analysis to determine the presence of the Aspergillus species. In another specific, non-limiting example, the same universal primers are used to amplify the identified sequences from *A. flavipes* (SEQ ID NOs: 10-12), *A. restrictus* (SEQ ID NOs: 13 and 14), *A. versicolor* (SEQ ID NOs: 15-18), *A. wentii* (SEQ ID NO: 19), and *A. chevalieri* (SEQ ID NOs: 20 and 21), or degenerate variants thereof, followed by sequence analysis to determine the presence of the Aspergillus species.

In an additional specific, non-limiting example, the Aspergillus ITS1 region is amplified using oligonucleotide primers of at least 15 consecutive nucleotides of the isolated ITS1 sequences from *A. clavatus* (SEQ ID NO: 1), *A. granulosus* (SEQ ID NOs: 2 and 3), *A. sydowii* (SEQ ID NOs: 4-9), *A. flavipes* (SEQ ID NOs: 10-12), *A. restrictus* (SEQ ID NOs: 13 and 14), *A. versicolor* (SEQ ID NOs: 15-18), *A. wentii* (SEQ ID NO: 19), and *A. chevalieri* (SEQ ID NOs: 20 and 21), followed by sequence differentiation (for example sequence analysis) to determine the presence of the Aspergillus species. Sequence analysis can include, for example, obtaining the sequence of the amplified ITS1 region, or using a probe to identify specific identifying sequences within the amplified ITS1 region. In particular embodiments, the probe or primer comprises at least 15 contiguous nucleotides, such as at least 18 contiguous nucleotides, for example 15-18 contiguous nucleotides, of the following sequences:

```
A. granulosus
CAGGTCTGCCCCTGGCAG      (SEQ ID NO: 33)
GTCTGCCCCTGGCAGGCC      (SEQ ID NO: 34)
TGCCCCTGGCAGGCCTAA      (SEQ ID NO: 35)
ACCGAACCTTCTTGTTTA      (SEQ ID NO: 36)
GAACCTTCTTGTTTAAGC      (SEQ ID NO: 37)
CCTTCTTGTTTAAGCCTG      (SEQ ID NO: 38)
TCTTGTTTAAGCCTGTTG      (SEQ ID NO: 39)
TGTTTAAGCCTGTTGTCT      (SEQ ID NO: 40)
TTAAGCCTGTTGTCTGAG      (SEQ ID NO: 41)
AGCCTGTTGTCTGAGCTT      (SEQ ID NO: 42)
CTGTTGTCTGAGCTTGAT      (SEQ ID NO: 43)
TTGTCTGAGCTTGATAGC      (SEQ ID NO: 44)
TCTGAGCTTGATAGCAAA      (SEQ ID NO: 45)
GAGCTTGATAGCAAATCT      (SEQ ID NO: 46)
CTTGATAGCAAATCTATTA     (SEQ ID NO: 47)
TTGTTTAAGCCTGTTGTC      (SEQ ID NO: 48)
TTTAAGCCTGTTGTCTGA      (SEQ ID NO: 49)

A. nidulans
TTTCATGCCTGAGAGTGA      (SEQ ID NO: 50)
CATGCCTGAGAGTGATGC      (SEQ ID NO: 51)
GCCTGAGAGTGATGCAGT      (SEQ ID NO: 52)
TGAGAGTGATGCAGTCTG      (SEQ ID NO: 53)
GAGTGATGCAGTCTGAGC      (SEQ ID NO: 54)
TGATGCAGTCTGAGCCTG      (SEQ ID NO: 55)
TGCAGTCTGAGCCTGAAT      (SEQ ID NO: 56)
AGTCTGAGCCTGAATACA      (SEQ ID NO: 57)
CTGAGCCTGAATACAAAT      (SEQ ID NO: 58)
AGCCTGAATACAAATCAG      (SEQ ID NO: 59)
CTGAATACAAATCAGTCA      (SEQ ID NO: 60)

A. ustus
CTGTCTTTAGTGTTGTCT      (SEQ ID NO: 61)
TCTTTAGTGTTGTCTGAG      (SEQ ID NO: 62)
TTAGTGTTGTCTGAGCTT      (SEQ ID NO: 63)
GTGTTGTCTGAGCTTGAT      (SEQ ID NO: 64)
TTGTCTGAGCTTGATAGC      (SEQ ID NO: 65)
GAGCTTGATAGCAAACCT      (SEQ ID NO: 66)
CTTGATAGCAAACCTATTA     (SEQ ID NO: 67)
```

In a further specific, non-limiting example, the *Aspergillus* ITS1 region is amplified using universal fungal primers ITS5 (SEQ ID NO: 28), ITS1 (SEQ ID NO: 31), ITS2 (SEQ ID NO: 29), and ITS4 (SEQ ID NO: 30), followed by hybridization with oligonucleotide probes comprising at least 15 consecutive nucleotides (for example 15-18 nucleotides) of an ITS1 region of SEQ ID NO: 1, SEQ ID NOs: 2 or 3, SEQ ID NOs: 4, 5, 6, 7, 8 or 9, SEQ ID NOs: 10, 11 or 12, SEQ ID NOs: 13 or 14, SEQ ID NOs: 15, 16, 17 or 18, SEQ ID NO: 19, or SEQ ID NOs: 20 and 21 to determine the presence of the *Aspergillus* species. In particular embodiments, the probe comprises at least 15 contiguous nucleotides, such as at least 18 contiguous nucleotides, of the above listed probe sequences.

IV. Kits

The oligonucleotide primers disclosed herein can be supplied in the form of a kit for use in detection of *Aspergillus*. In such a kit, one or more of the oligonucleotide primers is provided in one or more containers. An oligonucleotide primer can be provided suspended in an aqueous solution, or as a freeze-dried or lyophilized powder. The container(s) in which the oligonucleotide(s) are supplied can be any conventional container that is capable of holding the supplied form; e.g., microfuge tubes, ampoules, or bottles. In some applications, pairs of primers can be provided in pre-measured single use amounts in individual, typically disposable, tubes or equivalent containers. With such an arrangement, the sample to be tested for the presence of *Aspergillus* nucleic acids can be added to the individual tubes and amplification carried out directly, followed by sequence analysis.

In some embodiments, kits can also include the reagents necessary to carry out PCR amplification reactions, including DNA sample preparation reagents, appropriate buffers (e.g., polymerase buffer), salts (e.g., magnesium chloride), and deoxyribonucleotides (dNTPs). One or more control sequences for use in the PCR reactions can also be supplied in the kit.

In one embodiment, kits are supplied with instructions. In one specific, non-limiting example, the instructions are written instructions. In another such example, the instructions are contained in a videocassette or in a CD. The instructions may, for example, instruct the user how to use the primers to amplify the nucleic acid sequences, and then differentiate the species (and/or strains) of *Aspergillus* using the ITS1 sequences disclosed herein. In one specific non-limiting example, the instructions direct the user to sequence the amplified nucleic acid to detect sequence differences indicative of the different *Aspergillus*. Alternatively, probes may be used to detect the different sequences that are associated with each species or strain.

EXAMPLES

The following examples are provided to illustrate particular features of certain embodiments, but the scope of the claims should not be limited to those features exemplified.

Example 1

Materials and Methods

Isolation of Fungal DNA

*Aspergillus* isolates were grown on Czapek-Dox agar (Difco Laboratories, Detroit, Mich.) for 10 to 14 days at 25° C. and at 37° C. to confirm their purity, to identify species based on morphological and other traditional characteristics, and to generate fungal growth for DNA extraction.

Fungal biomass, scraped from the surface of one agar plate, was transferred into a pre-cooled (−20° C.) sterile ceramic mortar, overlayed with liquid nitrogen, and slowly ground with a pestle into a fine powder. The powder was suspended in 2 ml of G-2 buffer (Genomic DNA buffer set, Qiagen, Inc.) containing RNase (Sigma Chemical Co., St. Louis, Mo.), and transferred into an Oak Ridge centrifugation tube (Nalge Nunc International, Rochester, N.Y.). Following the addition of 45 µl of proteinase K solution (Roche Molecular Biochemicals, Indianapolis, Ind.), the suspension was incubated with intermittent agitation at 55° C. for 2 hours. The crude extract was centrifuged at 22,870×g for 10 minutes and the supernatant was transferred to a Falcon tube (Becton Dickinson, Franklin Lakes, N.J.), and briefly vortex-mixed. DNA was then purified using Genomic-tip 20/G columns (Qiagen, Inc.) according to the manufacture's instructions. The eluted DNA was supplemented with 2.5 µl of glycogen solution (Gentra Systems, Minneapolis, Minn.), precipitated by standard methods (see Sambrook et al.), and resuspended in 60 µl of DNA rehydration buffer (PureGene kit, Gentra Systems).

Extraction of *Aspergillus* DNA from Biological Samples 1 ml of a biological sample was incubated with 1 ml of lysis solution (1 N NaOH, 0.2 M sodium citrate, 0.4 M N-acetylcysteine) on a shaker at room temperature for 30 minutes. The sample was then centrifuged at 12,000 rpm for 10 minutes in a microfuge. The supernatant was removed, 2 ml of lysis solution was added, and the pellet was resuspended by vortexing for 30 seconds. The sample was again centrifuged at 12,000 rpm for 10 minutes in a microfuge. The supernatant was removed and the pellet was resuspended in 2 ml of 20 mM Tris-HCl (pH 8.3), followed by centrifugation at 12,000 rpm for 10 minutes in a microfuge. The supernatant was removed, 300 µl of sorbitol buffer (1 M sorbitol, 100 mM EDTA), 10 µl of β-mercaptoethanol, and 200 units of zymolyase were added, and the pellet was resuspended by briefly vortexing several times. The mixture was incubated at 35° C. for 1.5 hours on a shaker, followed by centrifugation at 6,000 rpm for 15 minutes in a microfuge. The supernatant was removed and the pellet resuspended in 2 ml of sorbitol buffer. The sample was again centrifuged at 6,000 rpm for 15 minutes in a microfuge. The supernatant was removed and the pellet was resuspended in 180 µl of ATL lysis buffer (Qiagen, Inc.). Following the addition of 20 µl of a proteinase K solution (Qiagen, Inc.), the sample was incubated at 55° C. for 1.5 hours on a shaker. The sample was then centrifuged at 8,000 rpm for 20 minutes in a microfuge. The supernatant was removed and the pellet was resuspended in 200 µl of 20 mM Tris-HCl (pH 8.3), followed by boiling in a water bath for 40 minutes. DNA was then purified using QIAamp DNA columns (Qiagen, Inc.) according to the manufacture's instructions.

Preparation of Primers and Probes

All primers and probes were synthesized by β-cyanoethyl phosphoramidite chemistry using a 394 or expedite automated DNA synthesizer (PE Applied Biosystems, Foster City, Calif.).

ITS3, a universal fungal sequence located in the 5.8S region of the fungal rDNA and contained within the region amplified by the ITS5 and ITS2 or ITS5 and ITS4 primers, was biotinylated at the 5' end by incorporating dimethyoxytrityl-biotin-carbon-6-phosphoramidite during its synthesis. This biotinylated probe (ITS3-B) was then purified by reverse phase liquid chromatography.

Digoxigenin-labeled probes were synthesized with a 5'-terminal amine group using 5' Amino-Modifier C6 (Glen Research, Sterling, Va.), mixed with a 10-fold molar excess of digoxigenin-3-O-methylcarbonyl-ε-aminocaproic acid N-hydroxysuccinimide ester (Roche) in 0.1 M sodium carbonate buffer, pH 9.0, and incubated at ambient temperature overnight. The digoxigenin-labeled probes were then purified by reverse-phase high-pressure liquid chromatography, Becker, et al., *J. Chromatogr.* 326:293-299, 1985.

PCR Amplification of rDNA Internal Transcribed Spacer 1

The PCR reaction mix consisted of 10 mM Tris-HCl buffer containing 50 mM KCl, pH 8.0 (Roche), 1.5 mM $MgCl_2$ (Roche), 0.2 mM dNTPs (Roche) and 1.25 U Taq polymerase (Roche). Primers ITS5 and ITS2, or ITS5 and ITS4, were added to a final concentration of 20 pM each. Template DNA was added at a final concentration of 1 ng per 50 µl reaction mix. For each experiment, at least one reaction tube received water in place of template DNA as a negative control. Amplification was performed in a GeneAmp PCR System 9700 (PE Applied Biosystems). Initial denaturation of template DNA was achieved by heating at 95° C. for 5 minutes. This was followed by 30 cycles of 95° C. for 30 seconds, 58° C. for 30 seconds, and 72° C. for 1 minute. A final extension step was conducted for 5 minutes at 72° C. Appropriate controls were included and PCR contamination precautions were followed, Fujita et al., *J. Clin. Microbiol.* 33:962-67, 1995.

Sequence Analysis

PCR products generated with either primer pairs ITS5 and ITS2, ITS5 and ITS4, ITS1 and ITS2, or ITS1 and ITS4, were purified using the QIAquick PCR purification kit (Qiagen, Inc.) according to the manufacture's protocol. Purified products were sequenced on both strands using the same primers as initially used for PCR amplification, and the BigDye Termination Cycle Sequencing Ready Reaction Kit (PE Applied Biosystems) as recommended by the manufacturer. Cycle sequencing on a GeneAmp PCR System 9700 consisted of an initial denaturation at 96° C. for 5 minutes, followed by 30 cycles of 96° C. for 10 seconds, 50° C. for 5 seconds, and 60° C. for 4 minutes. Sequencing products were purified using the Dye-Ex Spin Kit (Qiagen, Inc.), dried in a vacuum centrifuge, and resuspended in formamide. Sequencing products were analyzed on an automated capillary DNA sequencer (ABI Prism 310 Genetic Analyzer, PE Applied Biosystems) according to the manufacturer's instructions. GenBank searches and comparative sequence analysis were assisted by the BLAST search tools, the Genetics Computer Group software package (University of Wisconsin, Madison), and the Clustal W alignment program (Thompson et al., *Nucleic Acids Research* 22:4673-80, 1994).

Example 2

Comparative Analysis of *Aspergillus* ITS1 Consensus Sequences

A total of 46 ITS1 consensus sequences ranging in length from 142 nucleotides (*A. chevalieri*) to 187 nucleotides (*A. clavatus*) were compiled (Table I). Overall, 5 regions with significant interspecies variability in length and sequence were recognized (FIG. 2). These hypervariable regions were defined as follows: ITS1-V1, position 8-30 (12-21 nucleotides in length); ITS1-V2, position 50-67 (13-14 nucleotides in length); ITS1-V3, position 81-141 (12-54 nucleotides in length); ITS1-V4, position 151-181 (23-28 nucleotides in length); and ITS1-V5, position 192-215 (17-21 nucleotides in length). Compared to the ITS1-V3 sequence of *A. niger* (54 nucleotides), notably shorter corresponding sequences were found for *A. chevalieri* (12 nucleotides), *A. granulosus* (21 nucleotides), *A. ustus* (21-30 nucleotides), *A. sydowii* (22 nucleotides), *A. versicolor* (22 nucleotides), and *A. nidulans* (21-22 nucleotides). In general, intraspecies diversity was ≦5 nucleotides and mainly present in the ITS1-V3 region, except for the very diverse *A. ustus* sequences. They differed from one another at a total of 33 positions within the ITS1-V1, -V3, -V4, and -V5 regions, thereby revealing two main types of *A. ustus* ITS1 sequences with characteristic nucleotides at positions 185, 202-204 and 215.

ITS1 sequence diversity enabled discrimination between *Aspergillus* species disclosed herein as estimated from comparisons between *A. nidulans* and closely related species (Table II). Sequence similarities of ≦77.3%, ≦80.5%, ≦95.4%, and ≦96.7% were determined for *A. nidulans* in comparison to *A. granulosus*, *A. ustus*, *A. sydowii*, and *A. versicolor*, respectively. *A. granulosus* compared to *A. ustus* exhibited moderate similarity (≦94.2%) whereas a high value of ≦98.1% resulted for *A. sydowii* compared to *A. versicolor*. Using the same algorithm, intraspecies similarities of 99.3%, 100%, ≧89.0%, 98.7%, and 99.4% were found for the strains representing *A. nidulans*, *A. granulosus*, *A. ustus*, *A. sydowii*, and *A. versicolor*, respectively. The broad range of intraspecies similarities for *A. ustus* (≧89.0-99.4%) clearly reflected the presence of very diverse ITS1 sequences among the strains investigated as described above.

Species differentiation can be particularly efficiently performed by comparing or detecting sequence differences in the five hypervariable regions of ITS1. These hypervariable regions correspond to residues 8 to 31, 50 to 67, 81 to 141, 151 to 181, and 192 to 215 of the ITS1 alignment sequence shown in FIG. 2, where dots symbolize identical nucleotides compared to the *A. niger* I sequence, and dashes indicate alignment gaps. For example, the first hypervariable region of the *A. niger* I sequence comprises the sequence C-GGG-----TC-CTTTGG------G; the second hypervariable region comprises the sequence TCTA--TTGT-ACCC--T; the third hypervariable region comprises the sequence -GCCCGCCGCT-TGTC----GGCCGCCGGGGGGGCGCCTCT--GC-CCCCCGGGCCCGTGCCC; the fourth hypervariable region comprises the sequence CCCAACAC--GAA-CACTGT--CTGAAAGCG-; and the fifth hypervariable region comprises the sequence GTT--GATTGAAT-GCAA-TCA-G.

TABLE I

Source and characterization of *Aspergillus* strains disclosed herein.

| | | ITS1 | |
|---|---|---|---|
| Species | Strain[a] | GenBank accession no. | Length (nt)[b] |
| *A. candidus* | NRRL 303 | AF453881 | 180 |
| | NRRL 312 | AF453882 | 180 |
| *A. chevalieri* | ATCC 16443 | AF453883 | 142 |
| | ATCC 24546 | AF453884 | 142 |
| *A. clavatus* | ATCC 9192 | | 187 |
| *A. flavipes* | ATCC 11013 | AF453886 | 185 |
| | ATCC 16805 | AF453887 | 184 |
| | ATCC 24487 | AF453888 | 185 |
| *A. flavus* | ATCC 11497 | AF453890 | 181 |
| | ATCC 34896 | AF453891 | 181 |
| | ATCC 44310 | AF453892 | 181 |
| | ATCC 64025 | AF453893 | 181 |

TABLE I-continued

Source and characterization of *Aspergillus* strains disclosed herein.

| | | ITS1 | |
|---|---|---|---|
| Species | Strain[a] | GenBank accession no. | Length (nt)[b] |
| A. fumigatus | ATCC 16903 | AF453895 | 184 |
| | CDC 2570 | AF453896 | 184 |
| A. granulosus | CBS 119.5A | AF453897 | 156 |
| | NRRL 1932 | AF453898 | 156 |
| A. nidulans | ATCC 16855 | AF453899 | 153 |
| | ATCC 64027 | AF453900 | 153 |
| | CDC 040487 | AF453924 | 154 |
| A. niger | ATCC 1015 | AF453901 | 185 |
| | ATCC 16404 | AF453902 | 185 |
| | ATCC 64028 | AF453903 | 185 |
| A. parasiticus | ATCC 56775 | AF453906 | 179 |
| A. restrictus | NRRL 148 | AF453907 | 181 |
| | NRRL 151 | AF453908 | 181 |
| A. sydowii | NRRL 250 | AF453909 | 155 |
| | NRRL 4768 | AF453910 | 155 |
| | CUH1[c] | AF453911 | 155 |
| | CUH2[c] | AF453912 | 155 |
| | CUH7[c] | AF453913 | 155 |
| | CUH8[c] | AF453914 | 155 |
| A. tamarii[d] | ATCC 64841 | AF453894 | 182 |
| A. terreus | ATCC 1012 | AF453915 | 186 |
| | ATCC 10029 | AF453916 | 186 |
| | ATCC 7860 | AF453917 | 186 |
| A. ustus | ATCC 14417 | AF453918 | 155 |
| | ATCC 16801 | AF453919 | 155 |
| | NRRL 275 | AF453920 | 161 |
| | NRRL 5077 | AF453921 | 172 |
| | CUH4[c] | AF453922 | 156 |
| | CUH5[c] | AF453923 | 172 |
| A. versicolor | ATCC 10072 | AF453925 | 155 |
| | NRRL 238 | AF453926 | 155 |
| | NRRL 239 | AF453927 | 155 |
| | CUH3[c] | AF453928 | 155 |
| A. wentii | NRRL 3650 | | 178 |

[a]ATCC, American Type Culture Collection, Manassas, Virg.; CBS, Centraalbureau voor Schimmelcultures, Utrecht, The Netherlands; CDC, Centers for Disease Control and Prevention, Atlanta, Ga.; NRRL, Agricultural Research Service (ARS) Culture Collection, Peoria, Ill.
[b]Number of nucleotides determined by sequence analysis.
[c]Clinical isolate, kindly provided by Dr. J. H. Shin, Department of Clinical Pathology, Chonnam University Medical School, Kwangju, South Korea.
[d]Deposited in ATCC as *A. flavus*.

TABLE II

ITS1 sequence similarities for *A. nidulans* and closely related species

| Organism[a] | | % Similarity with species/sequevar[b] | | | | | | | | | | | |
|---|---|---|---|---|---|---|---|---|---|---|---|---|---|
| | | | AU | | | | | AS | | AV | | AN | |
| Species | ITS1-Sequevar | AG | I | II | III | IV | V | I | II | I | II | I | II |
| A. granulosus (AG) | | 100 | | | | | | | | | | | |
| A. ustus (AU) | I | 93.5 | 100 | | | | | | | | | | |
| | II | 93.5 | 97.4 | 100 | | | | | | | | | |
| | III | 93.5 | 99.4 | 97.4 | 100 | | | | | | | | |
| | IV | 94.2 | 94.2 | 92.9 | 93.6 | 100 | | | | | | | |
| | V | 88.5 | 90.3 | 89.0 | 89.7 | 92.5 | 100 | | | | | | |
| A. sydowii (AS) | I | 73.3 | 73.5 | 70.0 | 72.4 | 69.5 | 62.6 | 100 | | | | | |
| | II | 73.3 | 73.5 | 77.9 | 72.4 | 70.8 | 63.2 | 98.7 | 100 | | | | |
| A. versicolor (AV) | I | 72.7 | 72.8 | 77.2 | 71.7 | 68.8 | 61.9 | 98.1 | 98.1 | 100 | | | |
| | II | 73.3 | 73.5 | 77.9 | 72.4 | 69.5 | 62.6 | 97.4 | 97.4 | 99.4 | 100 | | |
| A. nidulans (AN) | I | 75.3 | 75.5 | 79.2 | 75.5 | 71.7 | 63.4 | 95.4 | 95.4 | 96.1 | 96.7 | 100 | |
| | II | 77.3 | 76.8 | 80.5 | 75.7 | 71.2 | 64.3 | 94.8 | 94.8 | 95.5 | 96.1 | 99.3 | 100 |

Figure 2:
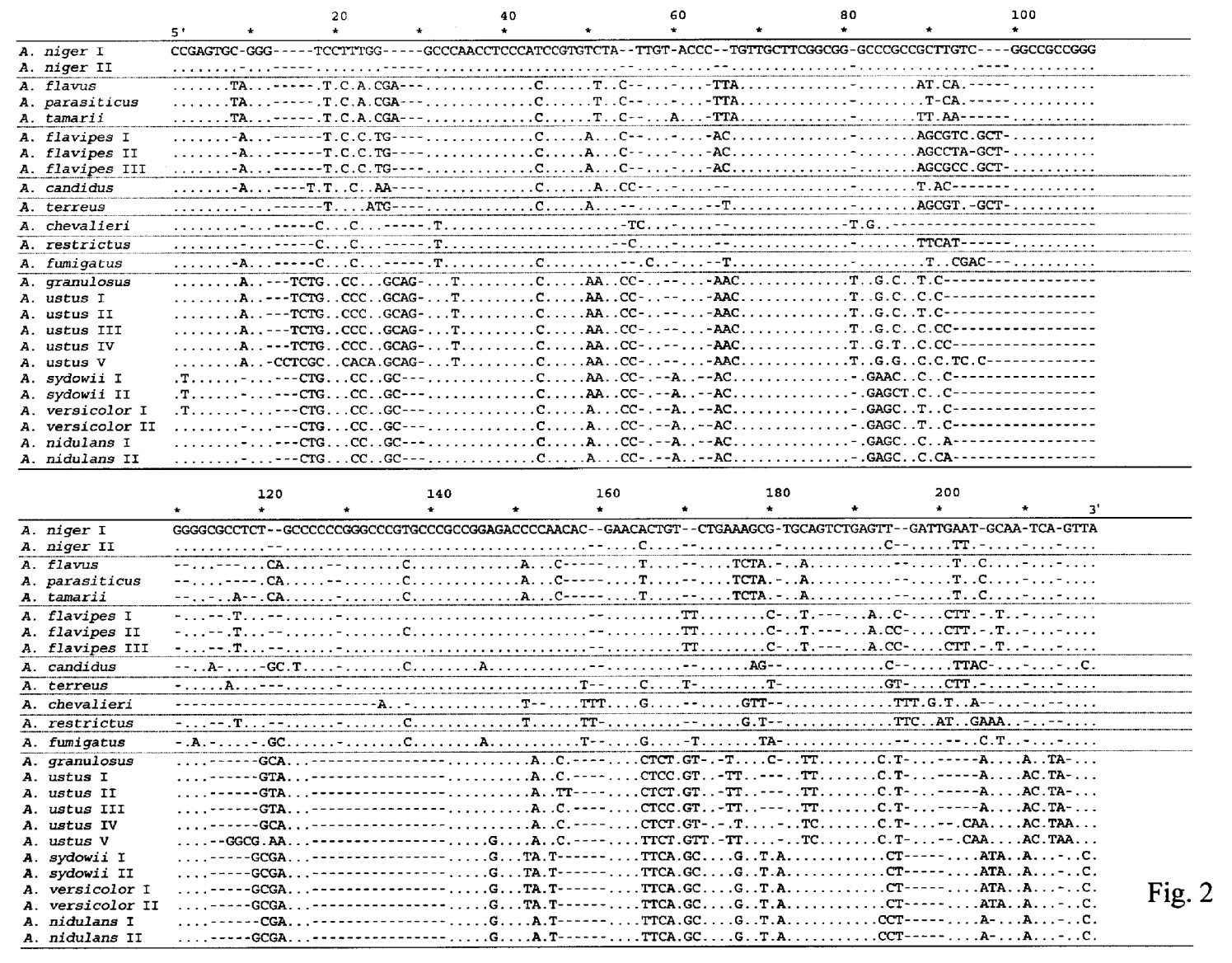

[a]Strains as listed in legend to FIG. 2.
[b]Similarities have been determined with complete ITS1 sequences as shown in FIG. 2 using the GAP algorithm (GCG).

Example 3

Polymerase Chain Reaction-Enzyme Immunoassay (EIA)

Enzyme immunoassay (EIA) identification of PCR products is performed as described in Elie et al., *J. Clin. Microbiol.* 36:3260-65, 1998 and Fujita et al., *J. Clin. Microbiol.* 33:962-67, 1995, with minor modifications.

Briefly, tubes containing 10 µl of heat-denatured (5 min at 95° C.) PCR products are placed on ice, and 200 µl of hybridization buffer (4×SSC, pH 7.0, 0.02M HEPES, 0.002M EDTA, 0.15% Tween 20) containing 10 ng of ITS3-B and 10 ng of a digoxigenin-labeled specific probe is added. Samples are mixed and incubated at 37° C. for 1 hour. 100 µl of the mixture is added in duplicate to each well of a streptavidin-coated (Roche), 96-well, microtiter plate and incubated at ambient temperature for 1 hour on a microtiter plate shaker (Labline Instruments, Melrose Park, Ill.) at ~350 rpm. Microtiter plates are washed 6 times with 0.01 M phosphate buffered saline, pH 7.2, containing 0.05% Tween 20 (PBST) before adding 100 µl of a 1:1000 dilution of horseradish peroxidase-labeled, anti-digoxigenin antibody (150 U/ml, Roche) per well. Plates are incubated for 1 hour at ambient temperature with shaking and then washed 6 times with PBST. 3,3',5,5'-Tetramethylbenzidine (TMB)-$H_2O_2$ substrate (Kirkegaard and Perry, Gaithersburg, Md.) is then added to the wells and the color reaction is allowed to develop at ambient temperature for 15 minutes. The optical density of each well is immediately read at a wavelength of 650 nm in a UVMax microtiter plate reader (Molecular Devices, Sunnyvale, Calif.). The optical density of the duplicate wells are averaged and converted to an EIA index (EI) which is calculated by dividing the optical density value of the wells which have received test DNA by the optical density of the PCR water control. An example of EIA identification of PCR products is shown in Table III.

Student's t test is used to determine differences between the mean EI of probe hybridization to homologous and heterologous DNA. Differences are considered significant when the value of P is less than or equal to 0.05.

TABLE III

Species specificities of DNA probes analyzed by hybridization with PCR products in an EIA

| Genomic DNA tested | EIA detection of PCR products with probe | | | | |
|---|---|---|---|---|---|
| | AG | AU | AS | AV | AN |
| A. granulosus (AG) | ++ | -- | -- | -- | -- |
| A. ustus (AU) | -- | ++ | -- | -- | -- |
| A. sydowii (AS) | | -- | ++ | -- | -- |
| A. versicolor (AV) | -- | -- | -- | ++ | -- |
| A. nidulans (AN) | | -- | -- | -- | ++ |

Example 4

DNA Sequence Based Identification of *Aspergillus* Species

This example illustrates how DNA based sequence identification can be used to identify different species of *Aspergillus*. A biological sample is obtained from an infected subject, and the fungus is cultured under conditions suitable for the growth of *Aspergillus*, followed by isolation of fungal DNA as described in Example 1, Isolation of Fungal DNA. Alternatively, the fungal DNA can be extracted directly from the biological sample as described in Example 1, Extraction of *Aspergillus* DNA from Biological Samples. The universal primer pairs ITS5 and ITS2, ITS5 and ITS4, ITS1 and ITS2, or ITS1 and ITS4 are added to the reaction mixture, as in Example 1, to amplify the fungal DNA present in the mixture, followed by sequence analysis as described in Example 1.

In one embodiment, following general amplification of the fungal DNA present in the sample using the universal primer pairs, specific primers from the hypervariable regions of ITS1 are used to amplify DNA from this region, and that DNA is subjected to DNA sequence analysis. In particular embodiments, the primer comprises at least 15 contiguous nucleotides, such as at least 18 contiguous nucleotides, of the primer sequences shown above (III. Method of Detecting *Aspergillus* ITS1 Sequences). This sequence information is compared to the fungal DNA sequences disclosed herein (SEQ ID NOs: 1-27), and a sequence match will confirm the identity of the *Aspergillus* species.

In yet another embodiment, general amplification of the fungal DNA present in the sample using the universal primer pairs is omitted, and specific primers from the hypervariable regions of ITS1 are used to amplify DNA from this region, and that DNA is subjected to DNA sequence analysis. In particular embodiments, the primer comprises at least 15 contiguous nucleotides, such as at least 18 contiguous nucleotides, of the primer sequences shown above (III. Method of Detecting *Aspergillus* ITS1 Sequences). This sequence information is compared to the fungal DNA sequences disclosed herein (SEQ ID NOs: 1-27), and a sequence match will confirm the identity of the *Aspergillus* species.

This technique has utility in rapidly and reliably identifying a single species of *Aspergillus* on a culture plate, in clinical specimens, in food, pharmaceuticals, and in environmental or other samples.

Example 5

Base Pair Differences Between Given Species by ITS or D1/D2 Region

The information in this Example illustrates that the inventors have found that there is substantial diversity between *Aspergillus* species in the ITS1 region, compared to the ITS2 region. This greater diversity allows the DNA sequence information to provide a better identification of the species. For example, there are approximately 48 base pair differences between *A. ustus* and *A. nidulans* in the ITS1 region, whereas there are only 6 base pair differences between these species in the ITS2 region.

The following Table IV illustrates the surprisingly superior ability of the ITS1 region to be informative about the identification of the *Aspergillus* species.

TABLE IV

Base Pair Differences Between Given Species by ITS or D1/D2 Region
Base pair differences between given species by ITS or D1/D2 region:

| Species | ITS1 | ITS2 | D1/D2 |
|---|---|---|---|
| *ustus* vs. *nidulans* | 48 | 6 | 3 |
| *sydowii* vs. *nidulans* | 9 | 9 | 7 |
| *granulosus* vs. *nidulans* | 52 | 10 | 4 |
| *granulosus* vs. *ustus* | 6 | 5 | 1 |
| *sydowii* vs. *versicolor* | 3 | 4 | 2 |
| *versicolor* vs. *nidulans* | 7 | 10 | 9 |
| *sydowii* vs. *ustus* | 40 | 7 | 9 |

TABLE IV-continued

Base Pair Differences Between Given Species by ITS or D1/D2 Region
Base pair differences between given species by ITS or D1/D2 region:

| Species | ITS1 | ITS2 | D1/D2 |
|---|---|---|---|
| *sydowii* vs. *candidus* | 93 | 24 | 20 |
| *niger* vs. *versicolor* | 90 | 29 | 15 |
| *niger* vs. *sydowii* | 93 | 26 | 15 |

The foregoing examples are provided by way of illustration only. One of skill in the art will appreciate that numerous variations on the nucleotide sequences and methods described herein can be employed to make and use oligonucleotide primers for the amplification of *Aspergillus* ITS1 sequences, and for their use in the detection and species identification of *Aspergillus*. We claim all such modifications and variations that fall within the scope and spirit of the claims below.

We claim:

1. A method of detecting the presence of an *Aspergillus* species in a biological sample, comprising:
   detecting the presence of an internal transcribed spacer 1 region nucleic acid molecule comprising:
   (a) SEQ ID NO: 1;
   (b) SEQ ID NO: 2 or 3;
   (c) SEQ ID NO: 4, 5, 6, 7, 8 or 9;
   (d) SEQ ID NO: 10, 11 or 12;
   (e) SEQ ID NO: 13 or 14;
   (f) SEQ ID NO: 15, 16, 17, or 18;
   (g) SEQ ID NO: 19; or
   (h) SEQ ID NO: 20 or 21,
   wherein (a) detects the presence of an *Aspergillus clavatus*; (b) detects the presence of an *Aspergillus granulosus*; (c) detects the presence of an *Aspergillus sydowii*; (d) detects the presence of an *Aspergillus flavipes*; (e) detects the presence of an *Aspergillus restrictus*; (f) detects the presence of an *Aspergillus versicolor*; (g) detects the presence of an *Aspergillus wentii*; and (h) detects the presence of an *Aspergillus chevalieri*.

2. The method of claim 1, comprising:
   amplifying a species internal transcribed spacer 1 region nucleic acid molecule comprising:
   (a) SEQ ID NO: 1;
   (b) SEQ ID NO: 2 or 3;
   (c) SEQ ID NO: 4, 5, 6, 7, 8 or 9;
   (d) SEQ ID NO: 10, 11 or 12;
   (e) SEQ ID NO: 13 or 14;
   (f) SEQ ID NO: 15, 16, 17, or 18;
   (g) SEQ ID NO: 19; or
   (h) SEQ ID NO: 20 or 21,
   and detecting the presence of an amplified nucleic acid molecule,
   wherein (a) detects the presence of an *Aspergillus clavatus*; (b) detects the presence of an *Aspergillus granulosus*; (c) detects the presence of an *Aspergillus sydowii*; (d) detects the presence of an *Aspergillus flavipes*; (e) detects the presence of an *Aspergillus restrictus*; (f) detects the presence of an *Aspergillus versicolor*; (g) detects the presence of an *Aspergillus wentii*; and (h) detects the presence of an *Aspergillus chevalieri*.

3. The method of claim 2, wherein amplifying an *Aspergillus* species internal transcribed spacer 1 region comprises the use of one or more oligonucleotide primers consisting of at least 15 and no more than 40 consecutive nucleotides of:
   (a) SEQ ID NO: 1;
   (b) SEQ ID NO: 2 or 3;
   (c) SEQ ID NO: 4, 5, 6, 7, 8 or 9;
   (d) SEQ ID NO: 10, 11 or 12;
   (e) SEQ ID NO: 13 or 14;
   (f) SEQ ID NO: 15, 16, 17, or 18; (g) SEQ ID NO: 19; or (h) SEQ ID NO: 20 or 21, and detecting the presence of an amplified nucleic acid molecule, wherein (a) detects the presence of an *Aspergillus clavatus*; (b) detects the presence of an *Aspergillus granulosus*; (c) detects the presence of an *Aspergillus sydowii*; (d) detects the presence of an *Aspergillus flavipes*; (e) detects the presence of an *Aspergillus restrictus*; (f) detects the presence of an *Aspergillus versicolor*; (g) detects the presence of an *Aspergillus wentii*; and (h) detects the presence of an *Aspergillus chevalieri*, wherein the one or more oligonucleotide primers are labeled or unlabeled.

4. The method of claim 3, wherein the oligonucleotide primer consists of at least 15 and no more than 40 consecutive nucleotides of SEQ ID NO: 1, and the method detects the presence of *Aspergillus clavatus*.

5. The method of claim 3, wherein the oligonucleotide primer consists of at least 15 and no more than 40 consecutive nucleotides of SEQ ID NO: 2 or 3, and the method detects the presence of *Aspergillus granulosus*.

6. The method of claim 3, wherein the oligonucleotide primer consists of at least 15 and no more than 40 consecutive nucleotides of SEQ ID NO: 4, 5, 6, 7, 8 or 9, and the method detects the presence of *Aspergillus sydowii*.

7. The method &claim 3, wherein the oligonucleotide primer consists of at least 15 and no more than 40 consecutive nucleotides of SEQ ID NO: 10, 11 or 12 and the method detects the presence of *Aspergillus flavipes*.

8. The method of claim 3, wherein the oligonucleotide primer consists of at least 15 and no more than 40 consecutive nucleotides of SEQ ID NO: 13 or 14, and the method detects the presence of *Aspergillus restrictus*.

9. The method of claim 3, wherein the oligonucleotide primer consists of at least 15 and no more than 40 consecutive nucleotides of SEQ ID NO: 15, 16, 17 or 18, and the method detects the presence of an *Aspergillus versicolor*.

10. The method of claim 3, wherein the oligonucleotide primer consists of at least 15 and no more than 40 consecutive nucleotides of SEQ ID NO: 19, and the method detects the presence of *Aspergillus wentii*.

11. The method of claim 3, wherein the oligonucleotide primer consists of at least 15 and no more than 40 consecutive nucleotides of SEQ ID NOs: 20 and 21, and the method detects the presence of *Aspergillus chevalieri*.

12. The method of claim 2, wherein detecting the presence of an amplified nucleic acid molecule comprises sequencing the nucleic acid molecule.

13. The method of claim 2, wherein the amplifying the internal transcribed spacer 1 region nucleic acid molecule comprises use of polymerase chain reaction (PCR).

14. The method of claim 2, wherein amplifying the internal transcribed spacer 1 region comprises the use of universal primers.

15. The method of claim 2, further comprising hybridizing the amplified nucleic acid molecule with a consisting of at least 15 and no more than 40 consecutive nucleotides of one of SEQ ID NOs: 1-21, thereby detecting the amplified nucleic acid molecule, wherein the probe is labeled or unlabeled.

16. A method of detecting the presence of an *Aspergillus versicolor* in a biological sample, comprising:

detecting the presence of an internal transcribed spacer 1 region nucleic acid molecule comprising SEQ ID NO: 16, thereby detecting Aspergillu *versicolor*.

17. The method of claim 3, wherein the one or more oligonucleotide primers consists of 15 to 18 consecutive nucleotides of one of:
(a) SEQ ID NO: 1;
(b) SEQ ID NO: 2 or 3;
(c) SEQ ID NO: 4, 5, 6, 7, 8 or 9;
(d) SEQ ID NO: 10, 11 or 12;
(e) SEQ ID NO: 13 or 14;
(f) SEQ ID NO: 15, 16, 17, or 18;
(g) SEQ ID NO: 19; or
(h) SEQ ID NO: 20 or 21.

18. The method of claim 15, further comprising hybridizing the amplified nucleic acid molecule with a probe consisting of at least 15 and no more than 40 consecutive nucleotides of one of SEQ ID NOs: 1-21, wherein the probe is labeled or unlabeled.

19. The method of claim 3, wherein at least one of the one or more oligonucleotide primers is labeled.

* * * * *

UNITED STATES PATENT AND TRADEMARK OFFICE
CERTIFICATE OF CORRECTION

| | | |
|---|---|---|
| PATENT NO. | : 7,871,779 B2 | Page 1 of 1 |
| APPLICATION NO. | : 12/115493 | |
| DATED | : January 18, 2011 | |
| INVENTOR(S) | : Morrison and Hinrikson | |

It is certified that error appears in the above-identified patent and that said Letters Patent is hereby corrected as shown below:

In the Claims:

Column 50, line 56 (Claim 7, line 1) "method &claim 3" should read -- method of claim 3 --.

Column 51, line 19 (Claim 15, line 2) "with a consisting of" should read -- with a probe consisting of --.

Signed and Sealed this
First Day of January, 2013

David J. Kappos
*Director of the United States Patent and Trademark Office*